(12) United States Patent
Halavee et al.

(10) Patent No.: US 12,268,863 B2
(45) Date of Patent: Apr. 8, 2025

(54) SHIFTABLE TRANSDUCER ARRAY WITH ANISOTROPIC MATERIAL LAYER

(71) Applicant: Novocure GmbH, Root (CH)

(72) Inventors: Noa Halavee, Tel Aviv (IL); Boaz Marsault, Haifa (IL); Elie Yaacobi, Haifa (IL); Golan Bar-Tal, Haifa (IL); Nitzan Shany, Haifa (IL); Yoram Wasserman, Haifa (IL); Stas Obuchovsky, Haifa (IL); Nataliya Kuplennik, Haifa (IL); David Shapiro, Haifa (IL); Dmitry Golom, Haifa (IL)

(73) Assignee: Novocure GmbH, Root (CH)

( * ) Notice: Subject to any disclaimer, the term of this patent is extended or adjusted under 35 U.S.C. 154(b) by 0 days.

(21) Appl. No.: 18/432,933

(22) Filed: Feb. 5, 2024

(65) Prior Publication Data
US 2024/0261566 A1 Aug. 8, 2024

Related U.S. Application Data

(60) Provisional application No. 63/615,891, filed on Dec. 29, 2023, provisional application No. 63/523,491, (Continued)

(51) Int. Cl.
*A61N 1/04* (2006.01)
*A61N 1/36* (2006.01)

(52) U.S. Cl.
CPC ......... *A61N 1/0476* (2013.01); *A61N 1/0496* (2013.01); *A61N 1/36002* (2017.08)

(58) Field of Classification Search
CPC ................ A61N 1/0476; A61N 1/0496; A61N 1/36002; A61N 1/403; A61B 2562/046;
(Continued)

(56) References Cited

U.S. PATENT DOCUMENTS 6,327,487 B1 12/2001 Stratbucker
6,376,393 B1 4/2002 Newton et al.
(Continued)

FOREIGN PATENT DOCUMENTS

CN 113577535 A 11/2021
KR 20070010908 A 1/2007
(Continued)

OTHER PUBLICATIONS

International Search Report and Written Opinion issued in International Application No. PCT/IB2022/062152 mailed Feb. 20, 2023.
(Continued)

*Primary Examiner* — Michael J Lau
*Assistant Examiner* — Anh-Khoa N Dinh
(74) *Attorney, Agent, or Firm* — McCarter & English, LLP; Michael A. Sartori

(57) ABSTRACT

A transducer apparatus for delivering tumor treating fields to a subject's body, the transducer apparatus including: an array of electrodes, the array configured to be positioned over the subject's body with a front face of the array facing the subject's body, the array comprising electrode elements positioned in existing electrode positions arranged around a centroid of the array; an anisotropic material layer electrically coupled to the array of electrodes and located on a front side of the front face of the array; and at least one void space in the array of electrodes capable of enclosing an areal footprint equivalent to at least a portion of an areal footprint of at least one existing electrode position, and superimposable on at least a portion of at least one existing electrode position by rotation of the array around the centroid.

20 Claims, 19 Drawing Sheets

Related U.S. Application Data filed on Jun. 27, 2023, provisional application No. 63/443,585, filed on Feb. 6, 2023.

(58) Field of Classification Search
CPC ............ A61B 10/0233; A61B 17/3403; A61B 2010/0208; A61B 2017/00026; A61B 2017/00199; A61B 2017/00438; A61B 2017/00796; A61B 2017/008; A61B 2017/3411; A61B 2017/3413; A61B 2090/306; A61B 2090/378; A61B 2562/0215; A61B 2562/0217; A61B 5/0536; A61B 90/17; A61B 90/36; A61B 90/37

See application file for complete search history.

(56) References Cited

U.S. PATENT DOCUMENTS

| | | | |
|---|---|---|---|
| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,333,852 | B2 | 2/2008 | Palti |
| 7,467,011 | B2 | 12/2008 | Palti |
| 7,519,420 | B2 | 4/2009 | Palti |
| 7,565,205 | B2 | 7/2009 | Palti |
| 7,565,206 | B2 | 7/2009 | Palti |
| 7,599,745 | B2 | 10/2009 | Palti |
| 7,599,746 | B2 * | 10/2009 | Palti ........................ C12N 13/00 607/76 |
| 7,706,890 | B2 | 4/2010 | Palti |
| 7,715,203 | B2 | 5/2010 | Choi |
| 7,715,921 | B2 | 5/2010 | Palti |
| 7,805,201 | B2 | 9/2010 | Palti |
| 7,890,183 | B2 | 2/2011 | Palti et al. |
| 7,912,540 | B2 | 3/2011 | Palti |
| 7,917,227 | B2 | 3/2011 | Palti |
| 8,019,414 | B2 | 9/2011 | Palti |
| 8,027,738 | B2 | 9/2011 | Palti |
| 8,170,684 | B2 | 5/2012 | Palti |
| 8,175,698 | B2 | 5/2012 | Palti et al. |
| 8,229,555 | B2 | 7/2012 | Palti |
| RE43,618 | E | 8/2012 | Palti |
| 8,244,345 | B2 | 8/2012 | Palti |
| 8,406,870 | B2 | 3/2013 | Palti |
| 8,447,395 | B2 | 5/2013 | Palti et al. |
| 8,447,396 | B2 | 5/2013 | Palti et al. |
| 8,465,533 | B2 | 6/2013 | Palti |
| 8,706,261 | B2 | 4/2014 | Palti |
| 8,718,756 | B2 | 5/2014 | Palti |
| 8,764,675 | B2 | 7/2014 | Palti |
| 9,023,090 | B2 | 5/2015 | Palti |
| 9,023,091 | B2 | 5/2015 | Palti |
| 9,039,674 | B2 | 5/2015 | Palti et al. |
| 9,056,203 | B2 | 6/2015 | Palti et al. |
| 9,440,068 | B2 | 9/2016 | Palti et al. |
| 9,655,669 | B2 | 5/2017 | Palti et al. |
| 9,750,934 | B2 | 9/2017 | Palti et al. |
| 9,910,453 | B2 | 3/2018 | Wasserman et al. |
| 10,188,851 | B2 | 1/2019 | Wenger et al. |
| 10,441,776 | B2 | 10/2019 | Kirson et al. |
| 10,779,875 | B2 | 9/2020 | Palti et al. |
| 10,967,167 | B2 | 4/2021 | Hagemann et al. |
| 11,103,698 | B2 | 8/2021 | Chang et al. |
| 11,191,956 | B2 | 12/2021 | Giladi et al. |
| 2004/0176804 | A1 | 9/2004 | Palti |
| 2005/0015134 | A1 | 1/2005 | Carim |
| 2006/0167499 | A1 | 7/2006 | Palti |
| 2006/0276858 | A1 | 12/2006 | Palti |
| 2007/0225766 | A1 | 9/2007 | Palti |
| 2007/0239213 | A1 | 10/2007 | Palti |
| 2009/0076366 | A1 | 3/2009 | Palti |
| 2010/0185078 | A1 | 7/2010 | Wilfinger et al. |
| 2012/0029419 | A1 | 2/2012 | Palti |
| 2012/0283726 | A1 | 11/2012 | Palti |
| 2013/0066412 | A1 | 3/2013 | Van Der Beek et al. |
| 2014/0330268 | A1 | 11/2014 | Palti et al. |
| 2017/0112983 | A1 | 4/2017 | Thorne et al. |
| 2017/0120041 | A1 | 5/2017 | Wenger et al. |
| 2017/0215939 | A1 | 8/2017 | Palti et al. |
| 2017/0281934 | A1 | 10/2017 | Giladi et al. |
| 2018/0001075 | A1 | 1/2018 | Kirson et al. |
| 2018/0001078 | A1 | 1/2018 | Kirson et al. |
| 2018/0008708 | A1 | 1/2018 | Giladi et al. |
| 2018/0050200 | A1 | 2/2018 | Wasserman et al. |
| 2018/0160933 | A1 | 6/2018 | Urman et al. |
| 2018/0202991 | A1 * | 7/2018 | Giladi ................ G01N 33/4836 |
| 2018/0280687 | A1 | 10/2018 | Carter et al. |
| 2019/0086741 | A1 * | 3/2019 | Milton ............. G02F 1/134309 |
| 2019/0117956 | A1 | 4/2019 | Wenger et al. |
| 2019/0117963 | A1 | 4/2019 | Travers et al. |
| 2019/0224474 | A1 | 7/2019 | Yang et al. |
| 2019/0308016 | A1 | 10/2019 | Wenger et al. |
| 2020/0001069 | A1 | 1/2020 | Kirson et al. |
| 2020/0009376 | A1 | 1/2020 | Chang et al. |
| 2020/0009377 | A1 | 1/2020 | Chang et al. |
| 2020/0016067 | A1 | 1/2020 | Gotlib et al. |
| 2020/0023179 | A1 | 1/2020 | Bomzon et al. |
| 2020/0061360 | A1 | 2/2020 | Hagemann et al. |
| 2020/0061361 | A1 | 2/2020 | Hagemann et al. |
| 2020/0069937 | A1 | 3/2020 | Naveh et al. |
| 2020/0078582 | A1 | 3/2020 | Alon et al. |
| 2020/0108031 | A1 | 4/2020 | Borst et al. |
| 2020/0114141 | A1 | 4/2020 | Bomzon et al. |
| 2020/0114142 | A1 | 4/2020 | Bomzon et al. |
| 2020/0121728 | A1 | 4/2020 | Wardak et al. |
| 2020/0129761 | A1 | 4/2020 | Bomzon et al. |
| 2020/0146586 | A1 | 5/2020 | Naveh et al. |
| 2020/0155835 | A1 | 5/2020 | Wasserman et al. |
| 2020/0171297 | A1 | 6/2020 | Kirson et al. |
| 2020/0179512 | A1 | 6/2020 | Giladi et al. |
| 2020/0219261 | A1 | 7/2020 | Shamir et al. |
| 2020/0269037 | A1 | 8/2020 | Hagemann et al. |
| 2020/0269041 | A1 | 8/2020 | Zeevi et al. |
| 2020/0269042 | A1 | 8/2020 | Giladi et al. |
| 2020/0368525 | A1 | 11/2020 | Maag et al. |
| 2021/0031031 | A1 | 2/2021 | Wasserman et al. |
| 2021/0038584 | A1 | 2/2021 | Voloshin-Sela |
| 2021/0060334 | A1 | 3/2021 | Avraham et al. |
| 2021/0069503 | A1 | 3/2021 | Tran et al. |
| 2021/0138233 | A1 | 5/2021 | Deslauriers |
| 2021/0162228 | A1 | 6/2021 | Urman et al. |
| 2021/0177492 | A1 | 6/2021 | Travers et al. |
| 2021/0185975 | A1 | 6/2021 | Strauss et al. |
| 2021/0187277 | A1 | 6/2021 | Wasserman et al. |
| 2021/0196348 | A1 | 7/2021 | Wasserman |
| 2021/0199640 | A1 | 7/2021 | Patel et al. |
| 2021/0203250 | A1 | 7/2021 | Wasserman |
| 2021/0268247 | A1 | 9/2021 | Story et al. |
| 2021/0299440 | A1 | 9/2021 | Deslauriers et al. |
| 2021/0308446 | A1 | 10/2021 | Alon et al. |
| 2021/0330950 | A1 | 10/2021 | Hagemann et al. |
| 2021/0346694 | A1 | 11/2021 | Wasserman et al. |
| 2021/0379362 | A1 | 12/2021 | Smith et al. |
| 2021/0408383 | A1 | 12/2021 | Kalra et al. |
| 2022/0095997 | A1 | 3/2022 | Wasserman |
| 2022/0096821 | A1 | 3/2022 | Kirson et al. |
| 2022/0096854 | A1 | 3/2022 | Carlson |
| 2022/0118249 | A1 | 4/2022 | Bomzon et al. |
| 2022/0161028 | A1 | 5/2022 | Giladi et al. |
| 2022/0193435 | A1 | 6/2022 | Wasserman et al. |
| 2022/0267445 | A1 | 8/2022 | Tran et al. |
| 2022/0280787 | A1 | 9/2022 | Bomzon et al. |
| 2022/0288395 | A1 | 9/2022 | Voloshin-Sela et al. |
| 2022/0305276 | A1 | 9/2022 | Marciano et al. |
| 2022/0313992 | A1 | 10/2022 | Wasserman |
| 2022/0323753 | A1 | 10/2022 | Voloshin-Sela et al. |
| 2022/0387784 | A1 | 12/2022 | Kirson et al. |
| 2022/0395699 | A1 | 12/2022 | Doyle |
| 2022/0409893 | A1 | 12/2022 | Wasserman et al. |
| 2023/0000384 | A1 | 1/2023 | Wasserman et al. |
| 2023/0001197 | A1 | 1/2023 | Wasserman et al. |
| 2023/0001221 | A1 | 1/2023 | Farber |

(56) References Cited

U.S. PATENT DOCUMENTS

| | | |
|---|---|---|
| 2023/0009366 A1 | 1/2023 | Voloshin-Sela et al. |
| 2023/0019638 A1 | 1/2023 | Wasserman |
| 2023/0037806 A1 | 2/2023 | Wasserman et al. |
| 2023/0043071 A1 | 2/2023 | Wasserman et al. |
| 2023/0065587 A1 | 3/2023 | Shnaiderman et al. |
| 2023/0098801 A1 | 3/2023 | Carlson |
| 2023/0141087 A1 | 5/2023 | Giladi et al. |
| 2023/0149704 A1 | 5/2023 | Wasserman et al. |
| 2023/0181899 A1 | 6/2023 | Halavee et al. |
| 2023/0181919 A1 | 6/2023 | Wendel et al. |
| 2023/0188055 A1 | 6/2023 | Wasserman |
| 2023/0302289 A1 | 9/2023 | Halavee et al. |
| 2024/0009475 A1 | 1/2024 | Halavee et al. |

FOREIGN PATENT DOCUMENTS

| | | |
|---|---|---|
| WO | WO-2014/110071 A2 | 7/2014 |
| WO | WO-2021/226353 A1 | 11/2021 |
| WO | 2022/2009964 A1 | 9/2022 |
| WO | WO-2023/100103 A1 | 6/2023 |
| WO | WO-2024/165920 A1 | 8/2024 |
| WO | WO-2024/165995 A1 | 8/2024 |

OTHER PUBLICATIONS

Unknown, "Omni-Wave by Flexcon," FLEXCON Healthcare, www.FLEXcon.com/OMNI-WAVE, 2023.

Unknown, "Skin Contact Applications—Electrodes & Wearables," FLEXcon, www.FLEXcon.com, 2023.

International Search Report issued in application No. PCT/IB2022/058124 dated Nov. 20, 2022.

Cornelia Wenger et al., "A Review on Tumor-Treating Fields (TTFields): Clinical Implications Inferred from Computational Modeling", IEEE Reviews in Biomedical Engineering, vol. 11, Feb. 13, 2018, pp. 195-207.

\* cited by examiner

SHIFTABLE TRANSDUCER ARRAY WITH ANISOTROPIC MATERIAL LAYER

CROSS-REFERENCE TO RELATED APPLICATIONS

This Application claims priority to U.S. Provisional Application No. 63/443,585, filed Feb. 6, 2023, U.S. Provisional Application No. 63/523,491, filed Jun. 27, 2023, and U.S. Provisional Application No. 63/615,891, filed Dec. 29, 2023, the contents of which are incorporated by reference herein in their entirety.

BACKGROUND

Tumor treating fields (TTFields) are low intensity alternating electric fields within the intermediate frequency range (for example, 50 kHz to 1 MHz), which may be used to treat tumors as described in U.S. Pat. No. 7,565,205. TTFields are induced non-invasively into a region of interest by transducers placed on the patient's body and applying alternating current (AC) voltages between the transducers. Conventionally, transducers used to generate TTFields include a plurality of electrode elements comprising ceramic disks. One side of each ceramic disk is positioned against the patient's skin, and the other side of each disc has a conductive backing. Electrical signals are applied to this conductive backing, and these signals are capacitively coupled into the patient's body through the ceramic discs. Conventional transducer designs include rectangular arrays of ceramic disks aligned with each other in straight rows and columns and attached to the subject's body via adhesive.

DESCRIPTION OF EMBODIMENTS

Figure 1:
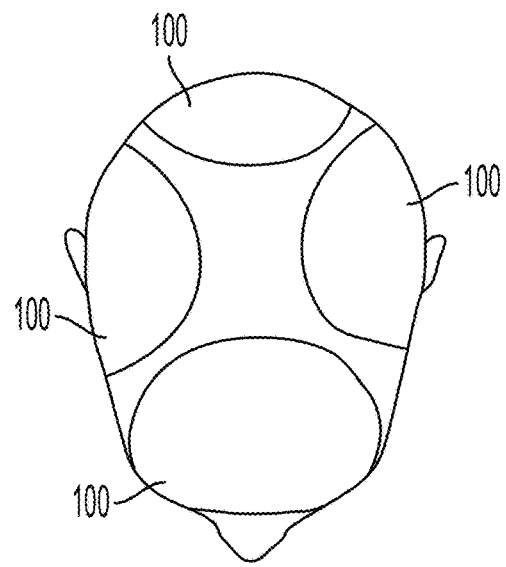
FIG. 1 depicts an example of transducers located on a subject's head.

This application describes exemplary transducer apparatuses used to apply TTFields to a subject's body, for example, for treating one or more cancers. This application also describes exemplary methods to apply TTFields to a subject's body using transducers.

Transducers used to apply TTFields to a subject's body often include multiple electrode elements electrically coupled together on a substrate and attached to the subject's body at a desired location, for example, via an adhesive backing of the substrate or a separately applied adhesive. Conventional transducers have large, rectangular surfaces so as to maximize a number of electrode elements that are located on the transducer for applying TTFields to the subject's body. However, subjects can experience skin irritation on portions of their skin that are contacted by the electrode elements during TTField treatment. Such irritation may be common at positions directly underneath the electrode elements, where heat and current may be at their highest concentrations, particularly for electrodes around the outer edge of the array.

As recognized by the inventors, on transducer arrays that comprise multiple electrode elements, the portions of the transducer arrays positioned directly beneath the electrode elements may become hotter than the portions of the transducer arrays positioned between the electrode elements. Furthermore, higher currents flow through the electrode elements that may be located along the edge of the array compared to the electrode elements located toward the middle of the array. Further still, an electrode element located at a corner or similar sharp bend in the edge of the array may have a higher current than other electrode elements along the edge and near the center of the array.

As recognized by the inventors, an uneven distribution of current through the transducer array may lead to higher temperature zones (or "hot spots"), e.g., at the corners or edges of the transducer array, which, in turn, may limit the maximum operational current that may be driven by a transducer array and, as a result, the strength of the resulting TTFields.

The inventors have now recognized that a need exists for transducers that can reduce, minimize, prevent, soothe, heal, or treat skin irritation without significantly changing the field intensity of TTFields being induced in the subject's body. For example, transducers that are able to be shifted so that skin previously contacted by electrode elements can be uncovered (or covered by a topical medication) without substantially moving the transducer from an optimal location on the subject's body are desired. The new position of the transducer after shifting is in substantially the same location if the footprint of the new position after shifting covers greater than or equal to 80% of the footprint of the original position before shifting; or if it covers greater than or equal to 90% of the footprint of the original position before shifting; or if it covers greater than or equal to 95% of the footprint of the original position before shifting. In some embodiments, the footprint of the new position of the transducer after shifting covers 100% of the footprint of the original position of the transducer before shifting. The shifting of the transducer apparatuses can reduce, minimize, prevent, soothe, heal, and/or treat skin irritation while maintaining the transducer in an optimal location on the subject's body. As a result, the transducers can continuously induce TTFields at an ideal location and power level for targeting a region of interest (e.g., tumor) in the subject's body, thereby improving patient outcomes.

The disclosed transducer apparatuses may be shifted via rotation about a centroid of the array of electrodes, or via translation of the array of electrodes, so that one or more portions of the subject's skin that were previously contacted by electrode elements may be uncovered (or covered by a medication), while maintaining an optimal location of the transducer on the subject's body. In some embodiments, the array of electrodes does not comprise an electrode position that encompasses the centroid of the array. The disclosed transducer apparatuses may have a substantially rounded shape enabling the transducers to be positioned on a subject's head. In other examples, the disclosed transducer apparatus may have other (e.g., non-rounded) shapes.

The disclosed transducer apparatuses may also include an anisotropic material layer located on a side of the array of electrode elements facing the subject's body. Such an anisotropic material layer may spread the heat and/or current generated at the individual electrode elements within a plane that is perpendicular to the direction from the electrode elements to the subject's body. Spreading heat and/or current in this plane may reduce the concentration of heat and/or current at locations directly under the individual electrode elements, thus reducing the amount or severity of irritation, if any, that occurs on the subject's skin. The transducer apparatus having an anisotropic material layer as described herein may also be shiftable (e.g., via rotation or translation) to further reduce, minimize, prevent, soothe, heal, and/or treat skin irritation.

Descriptions of embodiments related to specific exemplary Figures herein may be applicable, and may be combined with, descriptions of embodiments related to other exemplary Figures herein unless otherwise indicated herein or otherwise clearly contradicted by context.

FIG. 1 depicts transducers 100 positioned on the head of a subject's body. Such arrangement of transducers 100 is capable of applying TTFields to a tumor in a region of the subject's brain. Various other positions and/or orientations on the subject's head may be selected for placement of transducers. Each transducer 100 may have an array of electrode elements disposed thereon. Each transducer 100 may be placed on a subject's head with a face of the array of electrode elements facing and conforming to the subject's head. As illustrated, the transducers 100 on the subject's head do not overlap one another, e.g., due to their rounded shape.

Figure 2:
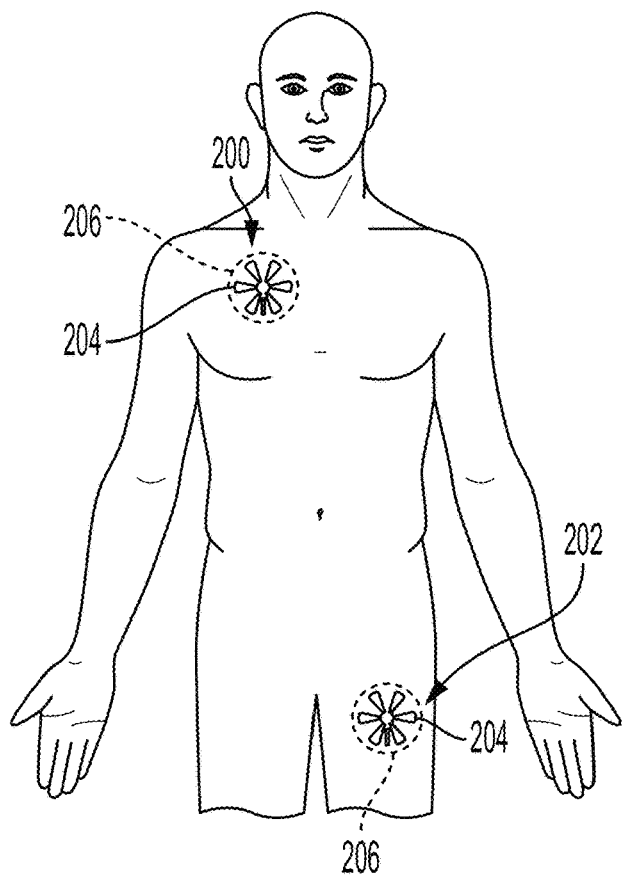
FIG. 2 depicts an example of transducers located on a subject's body.

FIG. 2 depicts transducers 200 and 202 attached to other portions (e.g., a thorax/torso and a thigh) of the subject's body. The transducers 200 and 202 may be affixed to the subject's body via a medically appropriate gel or adhesive. In other embodiments, the transducers 200 and 202 may be attached to one or more garments and held against the subject's body. Each of the transducers 200 and 202 may have an array of electrode elements 204 disposed thereon. Each transducer 200 and 202 may be placed over the subject's body with a face of the array of electrode elements facing and conforming to the subject's body.

Figure 8:
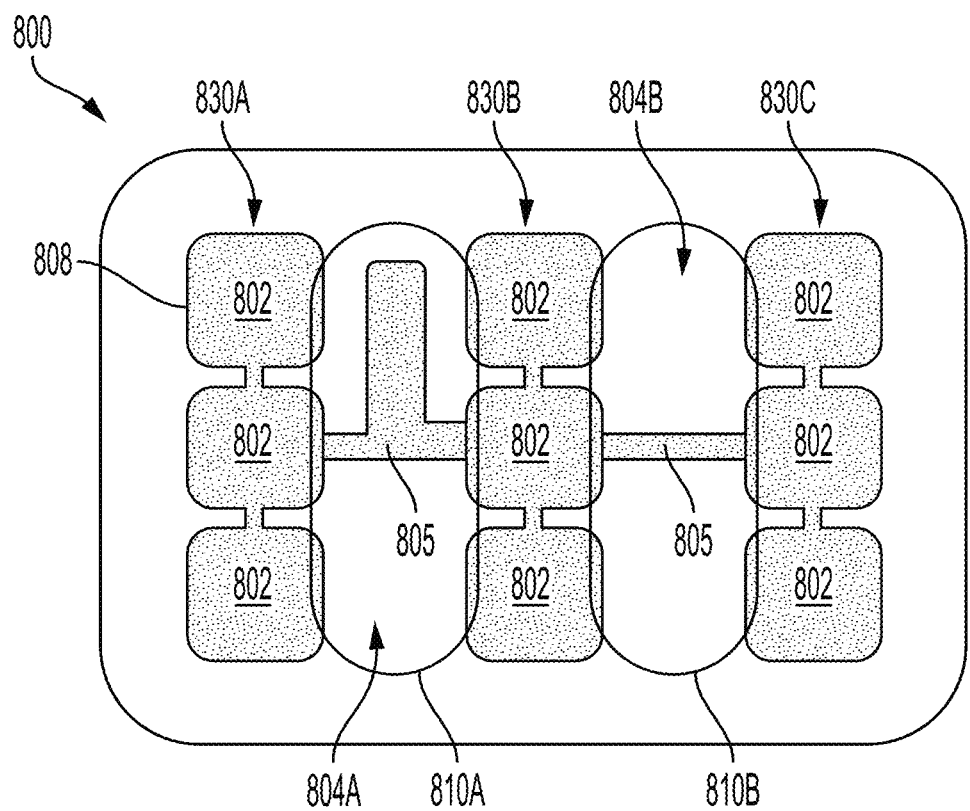
FIG. 8 depicts another example layout of an array of electrode elements and relief regions.

In the first transducer 200 and the second transducer 202, an outer perimeter 206 (defined by a dashed line in FIG. 2) traces the array of electrode elements 204. In an example, the outer perimeter 206 of the array on each transducer may have a substantially rounded edge. The outer perimeter 206 may be substantially circular, oval, ovaloid, ovoid, or elliptical in shape. For example, as illustrated, the outer perimeter 206 may have a circular shape. In another example, the outer perimeter 206 may have other shapes such as, for example, a square or rectangular shape or substantially square or rectangular shape with rounded corners (e.g., as shown in FIG. 8).

Figure 3A:
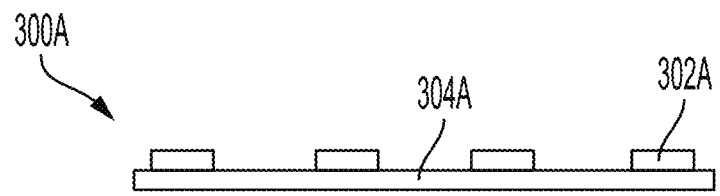
FIGS. 3A-3D are cross-sectional views of example structures of transducers.
Figure 3B:
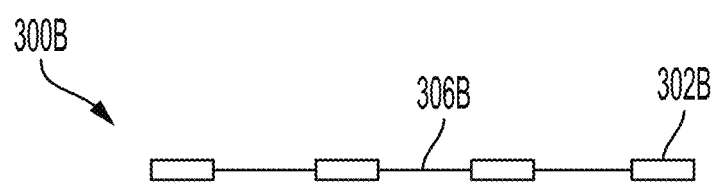

The structure of the transducers may take many forms. In FIG. 3A, the transducer 300A has a plurality of electrode elements 302A positioned on a substrate 304A. The substrate 304A is configured for attaching the transducer 300A to a subject's body. Suitable materials for the substrate 304A include, for example, cloth, foam, flexible plastic, and/or a conductive medical gel. The transducer 300A may be affixed to the subject's body via the substrate 304A (e.g., via an adhesive layer and/or a conductive medical gel). The adhesive layer that contacts the subject's skin may be present around the outer perimeter of the array of electrodes, and/or may be present between one or more gaps between electrodes. Alternatively, areas between electrodes may be non-adhesive regions. The transducer may be conductive or non-conductive. FIG. 3B depicts another example of the structure of the transducer 300B. In this example, the transducer 300B includes a plurality of electrode elements 302B that are electrically and mechanically connected to one another without a substrate. As an example, electrode elements 302B are connected to each other through conductive wires 306B.

Figure 3C:
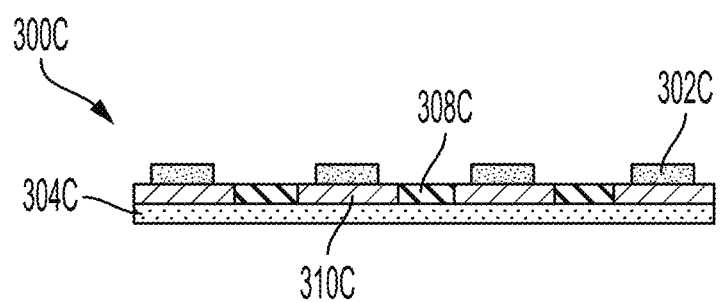
Figure 3D:
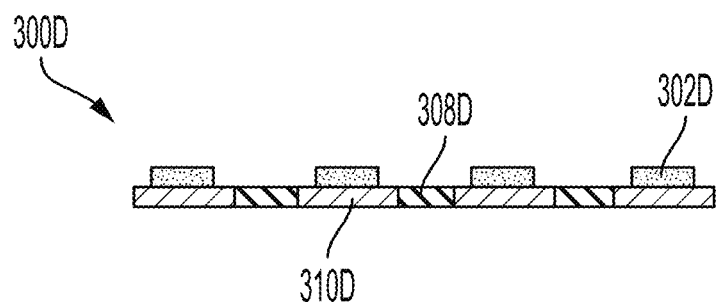

In FIGS. 3C and 3D, the transducers 300C and 300D include one or more medication regions 308C and 308D, respectively. The medication regions 308C and 308D may be non-adhesive regions. For example, no exposed adhesive is present in the medication region(s) 308C and 308D. The medication region(s) 308C and 308D may each comprise a medication substrate. The medication substrate may be capable of at least one of receiving, absorbing, or holding a topical medication applied thereto. The medication substrate may comprise a cloth, a gauze, a non-woven material, a foam, or a sponge located between one or more pairs of electrode elements 302C and 302D. As an example, the medication region(s) 308C and 308D may also comprise a topical medication integrated in or on the medication substrate. The topical medication may comprise a base component of oil, water, petrolatum, wax, cellulose, or a combination thereof. The topical medication may be a cream, an ointment, a lotion, a gel, a wax, a paste, or a mineral oil jelly. The topical medication may comprise at least one of an antibiotic, a steroid, an antiseptic, an emollient, an anesthetic, a terpene, a plant extract, a silicon-based organic polymer, an antifungal agent, a burn relief agent, a skin repair agent, an astringent, or an antihistamine. The topical medication may be any desired compound capable of soothing, healing, and/or providing relief for inflammation, sores, or other irritation that may develop on the skin of the subject's body. The topical medication may be substantially evenly distributed through a thickness of the medication substrate to form the medication regions 308C and 308D. Alternatively, the topical medication may be substantially disposed on the surface of the medication substrate to form the medication regions 308C and 308D.

As shown in FIG. 3C, the transducer 300C may include a transducer substrate 304C that is separate from the medication region(s) 308C. The array of electrode elements 302C may be disposed on a surface of the transducer substrate 304C, and the transducer substrate 304C may include an adhesive layer 310C for attaching the transducer apparatus to the subject's body. The medication substrate may be a portion of the transducer substrate 304C, or may be disposed on the surface of the transducer substrate 304C. Thus, the medication region 308C may be disposed on the surface of the transducer substrate 304C (as shown in FIG. 3C). In other embodiments, for example as shown in FIG. 3D, the transducer 300D may not include a transducer substrate, but rather merely an adhesive layer 310D for attaching the transducer 300D to the subject's body, and the medication region(s) 308D may be coupled between different portions of the adhesive layer 310D and span a distance between the electrode elements 302D.

The transducers 300A, 300B, 300C, 300D, and 300E may comprise arrays of substantially flat electrode elements 302A, 302B, 302C, 302D, and 302E, respectively. The array of electrode elements may be capacitively coupled. The electrode elements 302A, 302B, 302C, 302D, and 302E may be non-ceramic dielectric materials positioned over a plurality of flat conductors such as, for example, polymer films disposed over pads on a printed circuit board or over flat pieces of metal. In another example, the electrode elements 302A, 302B, 302C, 302D, and 302E are ceramic elements. In another example, the electrode elements do not have a dielectric material.

In some embodiments, the dielectric material of the electrode elements 302A, 302B, 302C, 302D, and 302E may have a dielectric constant ranging from 10 to 50,000. In some embodiments, the layer of dielectric material comprises a high dielectric polymer material such as poly (vinylidene fluoride-trifluoroethylene-chlorotrifluoroethylene) and/or poly(vinylidene fluoride-trifluoroethylene-1-chlorofluoroethylene). Those two polymers are abbreviated herein as "Poly(VDF-TrFE-CTFE)" and "Poly(VDF-TrFE-CFE)," respectively. The dielectric constant of these materials is on the order of 40. In some embodiments, the polymer layer may be poly(vinylidene fluoride-trifluoroethylene-chlorotrifluoroethylene-chlorofluoroethylene) or "Poly(VDF-TrFE-CTFE-CFE)."

In some embodiments, the layer of dielectric material of the electrode elements 302A, 302B, 302C, 302D, and 302E comprises a terpolymer comprising polymerized units of monomers such as VDF, TrFE, CFE and/or CTFE in any suitable molar ratio. Suitable terpolymers include those, for example, having 30 to 80 mol % VDF, 5 to 60 mol % TrFE, with CFE and/or CTFE constituting the balance of the mol % of the terpolymer.

Figure 3E:
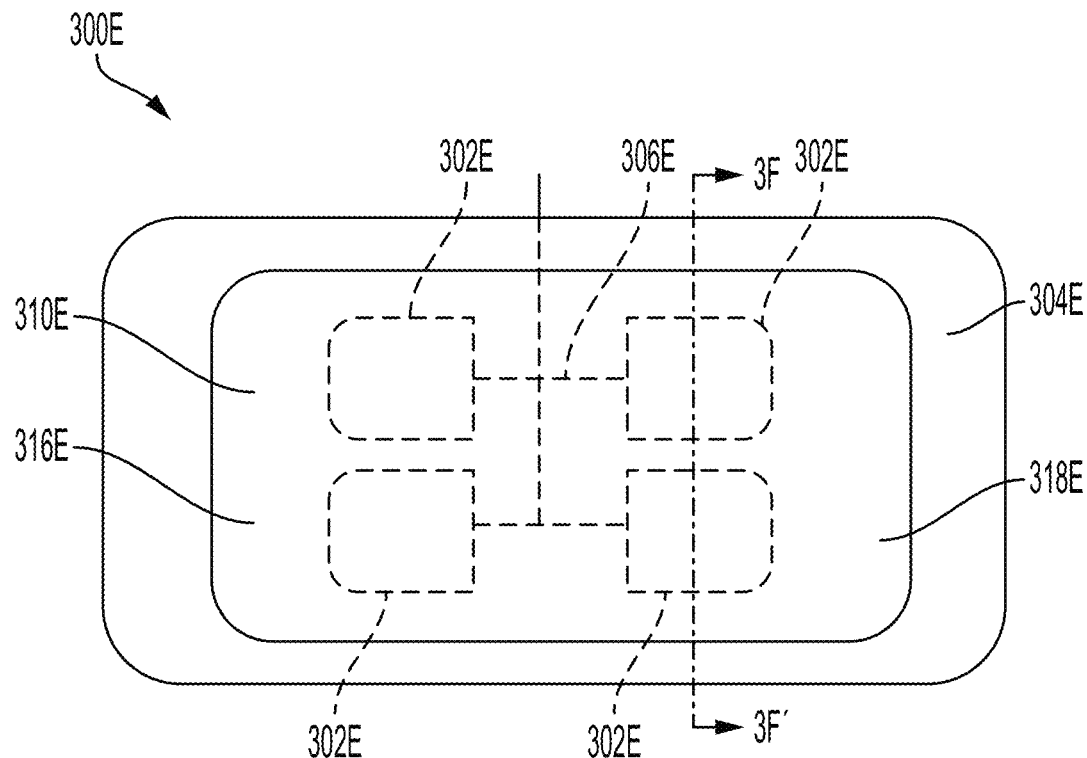
FIGS. 3E and 3F are top and cross-sectional views, respectively, of another example structure of a transducer.
Figure 3F:
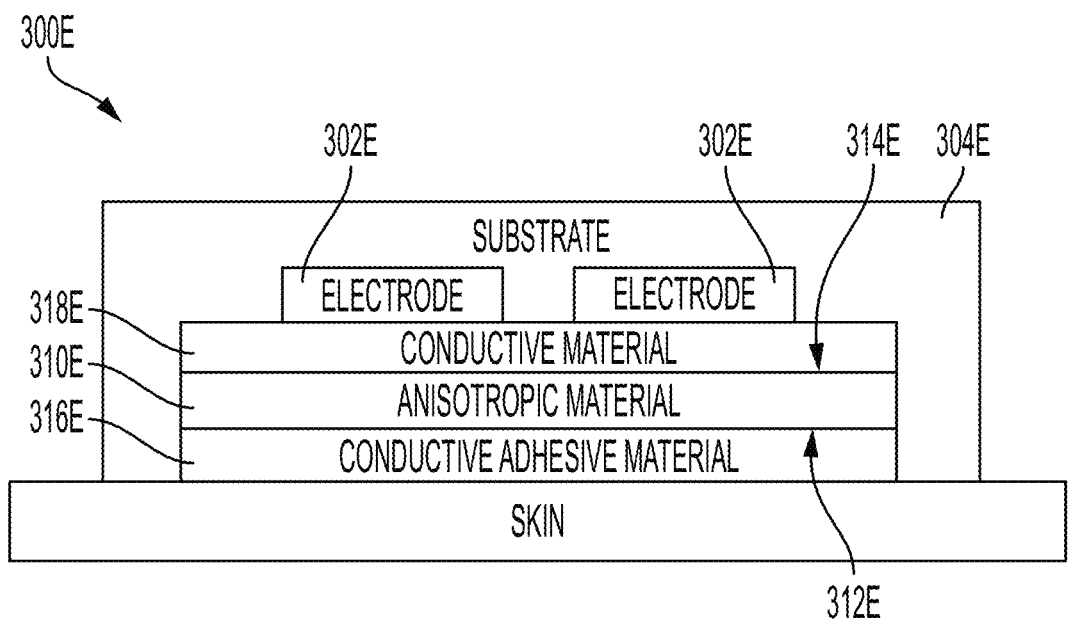

FIGS. 3E and 3F depict another example transducer 300E, where FIG. 3F is a cross-sectional view of FIG. 3E, taken across the section 3F-3F'. The transducer 300E includes a plurality of electrode elements 302E positioned on a substrate 304E, similar to the substrate 304A described above with reference to FIG. 3A. The substrate 304E is configured for attaching the transducer 300E to a subject's body. The electrode elements 302E may be connected to each other through conductive wires 306E.

Optionally, as shown in FIGS. 3E and 3F, embodiments described herein may incorporate into the transducer 300E an anisotropic material layer 310E. As shown, the anisotropic material layer 310E has a front face 312E and a back face 314E, wherein the back face 314E faces the array of electrode elements 302E. The anisotropic material layer 310E has anisotropic thermal properties and/or anisotropic electrical properties. If the anisotropic material layer 310E has anisotropic thermal properties (for example, greater thermal conductivity in the plane of the layer than through the plane of the layer), then the layer spreads the heat out more evenly over a larger surface area. If the anisotropic material layer 310E has anisotropic electrical properties (for example, greater electrical conductivity in the plane of the layer than through the plane of the layer), then the layer spreads the current out more evenly over a larger surface area. In each case, this lowers the temperature of the hot spots and raises the temperature of the cooler regions when a given AC voltage is applied to the array of electrode elements. Accordingly, the current may be increased (thereby increasing the therapeutic effect) without exceeding the safety temperature threshold at any point on the subject's skin.

In some embodiments, the anisotropic material layer 310E is anisotropic with respect to electrical conductivity properties. In some embodiments, the anisotropic material layer 310E is anisotropic with respect to thermal conductivity properties. In some preferred embodiments, the anisotropic material layer 310E is anisotropic with respect to both electrical conductivity properties and thermal conductivity properties.

The anisotropic thermal properties include directional thermal properties. Specifically, the anisotropic material layer 310E may have a first thermal conductivity in a direction that is perpendicular to its front face (skin-facing surface) 312E that is different from a thermal conductivity of the anisotropic material layer 310E in directions that are parallel to the front face 312E. For example, the thermal conductivity of the anisotropic material layer 310E in directions parallel to the front face 312E is more than two times higher than the first thermal conductivity. In some preferred embodiments, the thermal conductivity in the parallel directions is more than ten times higher than the first thermal conductivity. For example, the thermal conductivity of the sheet in directions that are parallel to the front face 312E may be more than: 1.5 times, 2 times, 3 times, 5 times, 10 times, 20 times, 100 times, 200 times, or even more than 1,000 times higher than the first thermal conductivity.

The anisotropic electrical properties include directional electrical properties. Specifically, the anisotropic material layer 310E may have a first electrical conductivity (or, conversely, resistance) in a direction that is perpendicular to its front face 312E that is different from an electrical conductivity (or resistance) of the anisotropic material layer 310E in directions that are parallel to the front face 312E. For example, the resistance of the anisotropic material layer 310E in directions parallel to the front face 312E may be less than the first resistance. In some preferred embodiments, the resistance in the parallel directions is less than half of the first resistance or less than 10% of the first resistance. For example, the resistance of the anisotropic material layer 310E in directions that are parallel to the front face 312E may be less than: 75%, 50%, 40%, 30%, 20%, 10%, 5%, 1%, 0.5%, or even less than 0.1% of the first resistance.

In some embodiments (e.g., when the anisotropic material layer 310E is a sheet of pyrolytic graphite), the anisotropic material layer 310E has both anisotropic electrical properties and anisotropic thermal properties.

The anisotropic material layer 310E may comprise graphite (e.g., a sheet of graphite). Examples of suitable forms of graphite include synthetic graphite, such as pyrolytic graphite (including, but not limited to, Pyrolytic Graphite Sheet (PGS), available from Panasonic Industry, Kadoma, Osaka, Japan), other forms of synthetic graphite, including but not limited to, graphite foil made from compressed high purity exfoliated mineral graphite (including, but not limited to, that supplied as MinGraph® 2010A Flexible Graphite, available from Mineral Seal Corp., Tucson, Arizona, USA), or graphitized polymer film, e.g., graphitized polyimide film, (including, but not limited to, that supplied by Kaneka Corp., Moka, Tochigi, Japan). In alternative embodiments, conductive anisotropic materials other than graphite may be used instead of graphite.

In some embodiments, the anisotropic material layer 310E is a sheet of pyrolytic graphite. Thermal conductivity of pyrolytic graphite sheets in directions that are parallel to the front face 312E of those sheets is typically more than 50 times higher than the thermal conductivity of those sheets in directions that are perpendicular to the front face 312E. Electrical resistivity of pyrolytic graphite sheets in directions that are parallel to the front face 312E of those sheets is typically less than 2% of the electrical resistivity of those sheets in directions that are perpendicular to the front face 312E.

The transducer 300E may further include at least one layer of conductive adhesive material 316E disposed on a front facing side of the anisotropic material layer 310E. In some embodiments, the at least one layer of conductive adhesive material 316E may be disposed on the front face 312E of the anisotropic material layer 310E. The at least one layer of conductive adhesive material 316E may have a biocompatible front surface. Note that in the embodiment illustrated in FIG. 3F, there is only a single layer of conductive adhesive material 316E, and that single layer (the front layer) is biocompatible. In alternative embodiments, there are more than one layer of conductive adhesive material 316E, in which case only the front layer may be biocompatible, or the front layer and one or more other layers may be biocompatible. In the FIG. 3F embodiment, the front layer of conductive adhesive material 316E is configured to ensure good electrical contact between the device and the body. In some embodiments, the front layer of conductive adhesive material 316E may cover the entire front face 312E of the anisotropic material layer 310E. The front layer of conductive adhesive material 316E may be the same size or larger than the anisotropic material layer 310E. In some embodiments, the front layer of conductive adhesive material 316E comprises hydrogel. In these embodiments, the hydrogel may have a thickness between 50 and 2,000 µm. In other embodiments, the front layer of conductive adhesive material 316E comprises a conductive adhesive composite as further disclosed herein.

The transducer 300E may further include a first layer of conductive material 318E positioned between the array of electrode elements 302E and the back face 314E of the anisotropic material layer 310E facing the array. The first layer of conductive material 318E facilitates the electrical contact between the array of electrode elements 302E and the back face 314E of the anisotropic material layer 310E. In some embodiments, the layer of conductive material 318E is a layer of hydrogel. In other embodiments, a different conductive material (e.g., conductive grease, conductive adhesives, conductive tape, etc.) could be used. For example, the layer of conductive material 318E may comprise a conductive adhesive composite as further disclosed herein.

In some embodiments, the at least one layer of conductive adhesive material 316E and/or the layer of conductive material 318E is a single layer of non-hydrogel conductive adhesive such as the developmental product FLX068983-FLEXcon® OMNI-WAVE™ TT 200 BLACK H-502 150 POLY H-9 44PP-8 from FLEXcon, Spencer, MA, USA, or other such OMNI-WAVE products from FLEXcon; or ARcare® 8006 electrically conductive adhesive composition manufactured and sold by Adhesives Research, Inc. (Glen Rock, PA, USA). Non-hydrogel conductive adhesives may comprise a waterless polymer with adhesive properties and carbon particles, powder, fibers, flakes, granules and/or nanotubes. The adhesive polymer may be, for example, an acrylic polymer or a silicone polymer, or combination thereof, which may be available as acrylic- or silicone-based carbon-filled adhesive tapes. The adhesive may additionally include one or more conductive polymers (such as, for example, polyaniline (PANI), or poly(3,4-ethylenedioxythiophene) (PEDOT), or others known in the art). The conductive filler in the at least one layer of conductive adhesive material 316E or conductive material 318E may be non-metallic. In these embodiments, the conductive adhesive may have a thickness between 10 and 2,000 µm, such as, from 20 to 1,000 µm, or 30 to 400 µm.

In some embodiments, the transducer 300E may be constructed using a pre-formed 3-(or more) layer laminate comprising the conductive material 318E, the anisotropic material layer 310E, and the at least one layer of conductive adhesive material 316E. In some embodiments, the at least one conductive adhesive material 316E and the conductive material 318E are both conductive adhesive composites as described above, and the anisotropic material layer 310E is a thin sheet of synthetic graphite such as pyrolytic graphite, as described above. The at least one conductive adhesive material 316E and the conductive material 318E may be the same material or may be different. By way of example, in an embodiment, both the conductive adhesive material 316E and the conductive material 318E may comprise an acrylic polymer and a carbon powder filler; or both the conductive adhesive material 316E and the conductive material 318E may comprise an acrylic polymer and a carbon fiber filler. In another embodiment, the conductive adhesive material 316E comprises an acrylic polymer and a carbon fiber filler, and the conductive material 318E comprise an acrylic polymer and a carbon powder filler; or vice-versa. In other embodiments, one or both of the conductive adhesive material 316E and the conductive material 318E may be a hydrogel.

FIGS. 4A-7I illustrate examples of transducer apparatuses or, in some examples, arrays of electrode elements of transducer apparatuses that may be used to apply TTFields to a subject's body. Such transducer apparatuses may include a construction similar to those discussed above and/or described below, and the arrays of electrode elements may be incorporated into transducer apparatuses which may include a construction similar to those discussed above and/or described below. Each example transducer apparatus enables a simple rotation of the transducer to reposition at least one void region (which may be a non-adhesive void region formed in the electrode array, or, alternatively, at least one medication region as described above with reference to FIGS. 3C and 3D) over an area of the subject's skin that was previously covered by an electrode element. Positioning a void region over the area of the subject's skin that was previously covered by an electrode element allows this area of the subject's skin to "breathe" and recover from the prior contact it had with the electrode element used to induce TTFields. The relative positioning of electrode elements and void regions (or medication regions) disclosed herein may be used along with the anisotropic material layer (e.g., 310E of FIGS. 3E and 3F) described above to further reduce irritation of the subject's skin.

As some subjects experience skin irritation in response to prolonged interaction of the skin with the electrode elements used to induce TTFields, moving the transducer so that a void is positioned over an affected area of the subject's skin may help to minimize, reduce, or prevent irritation of the subject's skin throughout TTField treatment. In addition, positioning a medication region over the area of the subject's skin that was previously covered by an electrode element allows an application of a topical medication to this area of the subject's skin to soothe, heal, reduce inflammation or soreness, or otherwise improve the condition of the subject's skin. In addition, spreading heat and/or current in a plane perpendicular to the direction from the electrode elements to the subject's skin may allow for a reduction in the heat and/or current at any particular location above the subject's skin, thereby reducing overall skin irritation. Since the transducer apparatus may be rotated about a centroid of the array of electrodes, this allows the transducer to continue outputting TTFields from the same optimal location on the subject's body during treatment while providing relief and/or healing to areas of the subject's skin.

Figure 4A:
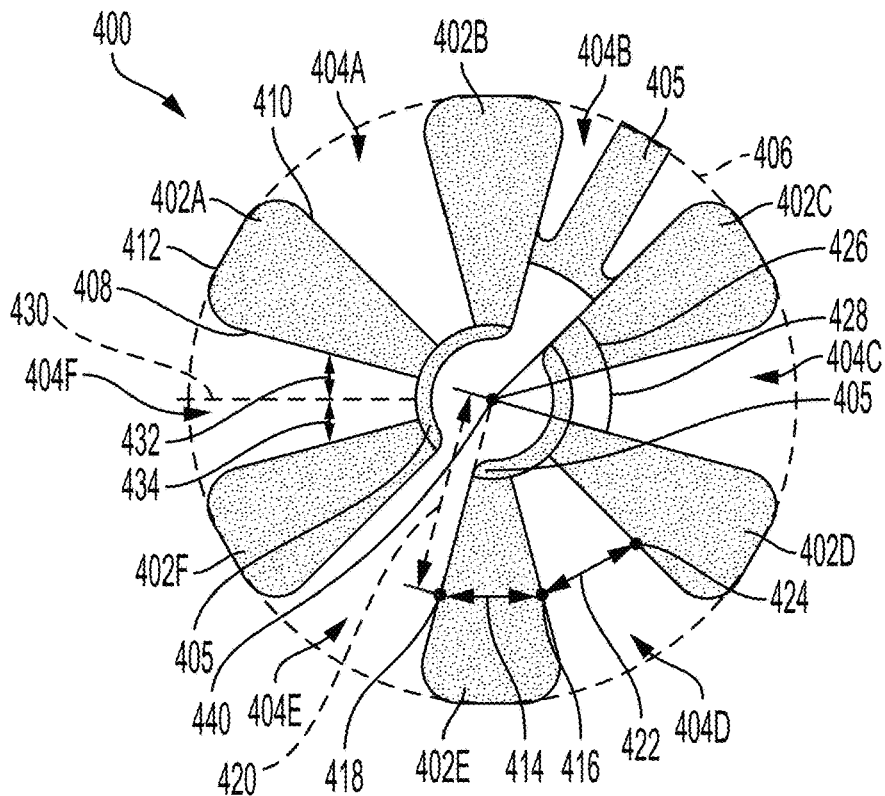
FIGS. 4A and 4B depict an example layout of an array of electrode elements on a transducer apparatus (FIG. 4A) and the array after rotation about its centroid (FIG. 4B).
Figure 4B:
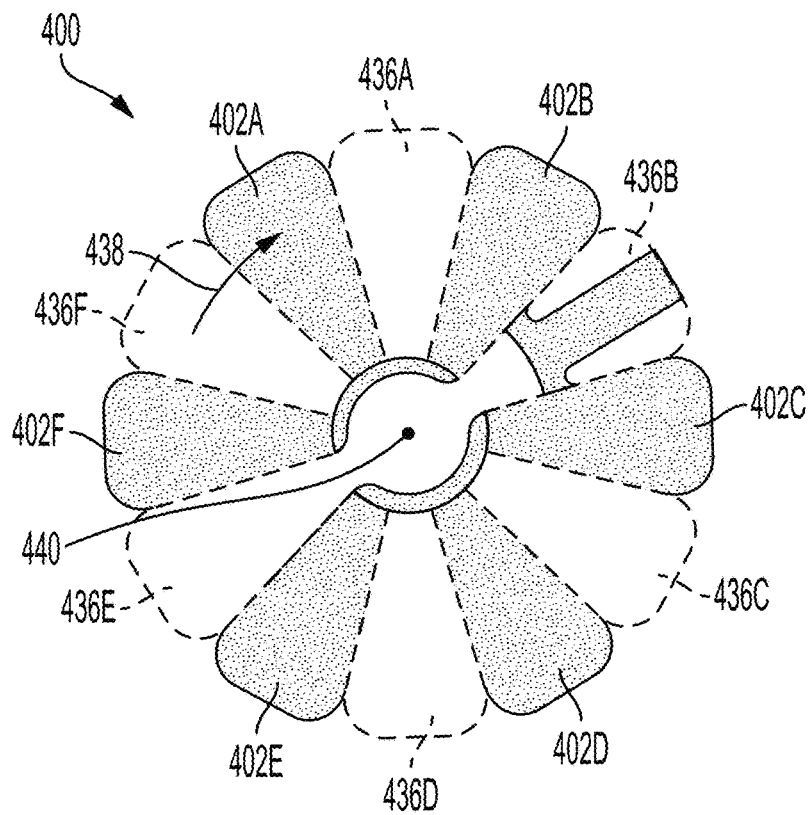

FIGS. 4A and 4B depict an example transducer apparatus 400, which may include an array of electrodes 402 (i.e., 402A-F) configured to be positioned over the subject's body with a face of the array facing the subject's body. FIGS. 4A and 4B illustrate the transducer apparatus 400 as viewed from a direction perpendicular to this face of the array. As shown in FIG. 4A, the transducer apparatus 400 may also include one or more blank spaces 404 (i.e., 404A-F), which do not overlap with any electrodes 402. At least part of one or more of the blank spaces 404 may be a relief region, defined herein as either 1) void regions of the transducer apparatus 400 that are fully uncovered or fully uncovered other than the transducer substrate and/or an anisotropic material layer (with or without conductive adhesive layer(s) (e.g., 316E) and/or a conductive layer (e.g., 318E)), or 2) non-adhesive regions comprising a medication substrate capable of receiving, absorbing, and/or holding a topical medication applied thereto, or 3) medication regions of the transducer apparatus comprising a medication substrate and a topical medication integrated therein or thereon used to administer a topical medication to an area of the subject's skin. These relief regions may optionally, have no exposed adhesive present. The topical medication may cover the entire surface of the medication substrate or may cover some portion of it; or it may be infused through some or the entire thickness of the medication substrate below the entire areal surface of the medication substrate or below an areal portion thereof; or it may be located in some combination of these. The areal footprint of the medication substrate may fill the entire area of the blank space or some portion thereof. In some embodiments, the medication region has a surface area sufficient enough to occupy at least 40%, or at least 50%, of the areal surface of one of the electrodes of the array of electrodes. In some embodiments, the medication region has a surface area sufficient enough to occupy at least 75%, or at least 95%, or at least 100%, of the areal surface of one of the electrodes of the array of electrodes. In some embodiments, the medication substrate is a portion of the transducer substrate. The array of electrodes 402 may be spaced about a centroid 440 of the array, and the blank spaces 404 may each be located between two adjacent electrodes. In some embodiments, the array of electrodes 402 comprises a number, x', of electrodes which may be arranged in Cx' rotational (point) symmetry about the centroid, where x' is an integer greater or equal to 2; or in some embodiments, greater or equal to 3. For example, the array of electrodes 402 may be arranged around the centroid in C3 symmetry, or C4 symmetry, or C5 symmetry, or C6 symmetry. In some embodiments, the transducer apparatus 400 has an alternating pattern of electrodes 402 and blank spaces 404.

In some embodiments, the transducer apparatus 400 has an alternating pattern of electrodes 402 and blank spaces 404. In other embodiments, non-alternating rotational patterns of electrodes 402 and blank spaces 404 may be used. The electrodes 402 may be electrically coupled together via one or more printed circuit board (PCB) layer(s)/connector(s) 405 or wire(s). The PCB layer(s)/connector(s) 405 (and 805 in FIG. 8) are not electrodes and are non-adhesive regions. Although six electrodes 402 and six blank spaces 404 are shown in FIGS. 4A and 4B, other embodiments may include different numbers of electrodes 402, blank spaces 404, or both in the array. For example, some embodiments include six electrodes 402 and three blank spaces 404 (FIG. 7C); other embodiments include five electrodes 402 and five blank spaces 404 (FIG. 7H); or four electrodes 402 and four blank spaces 404 (FIGS. 5B, 6F, and 7I); or three electrodes 402 and three blank spaces 404 (FIG. 6G).

The blank spaces 404 are present at one or more locations that correspond to, or may encompass, relative locations of one or more electrodes 402 upon rotation of the array about the centroid 440 by a first rotation amount (e.g., shown by arrow 438 in FIG. 4B). Upon rotation of the transducer apparatus 400 by a particular rotation amount (e.g., 30, 90, 150, 210, 270, or 330 degrees), the electrodes 402 are located (i.e., new positions shown in FIG. 4B) in areas that were previously (e.g., in FIG. 4A) occupied by the blank spaces 404 between adjacent electrodes 402. In addition, in the position of FIG. 4B, the blank spaces (of former positions 404 shown in FIG. 4A) between electrodes 402 are moved into locations 436 (i.e., 436A-F) that were previously occupied by the electrodes 402. This allows the skin that was previously in contact with or near the electrodes 402 to recover from exposure to the electrodes and/or receive a topical medication, thereby minimizing, reducing, preventing, soothing, healing, and/or treating skin irritation.

As shown in FIGS. 4A and 4B, each electrode 402 of the array may extend in a substantially radial direction (e.g., extending radially outward) away from the centroid 440 of the array. In addition, a centroid of each electrode 402 may be spaced substantially equidistant from the centroid 440 of the array. Each electrode 402 may have a substantially similar shape, and the blank space 404 between two electrodes 402 may have a size sufficient enough to occupy an electrode 402 therein. The electrodes 402 may be spaced substantially equidistant from each other about the centroid 440 of the array. Each electrode 402 may include (as shown with respect to electrode 402A) a first edge 408 extending in a radially outward direction relative to a center portion of the array and a second edge 410 extending in a radially outward direction relative to the center portion of the array. The electrode (e.g., 402A) may further include a rounded edge 412 connecting the first edge 408 to the second edge 410 at an end of the electrode 402A located radially away from the center portion. An outer perimeter 406 substantially tracing the array of electrodes 402 may have a circular shape, although other shapes may be possible (e.g., oval or ellipsoid in FIGS. 7H and 7I; or rectangular in FIGS. 6D, 6E and 8; or rounded triangular in FIG. 6G). In some embodiments described herein, there is no electrode positioned at the centroid, or overlapping the centroid, of the array of electrodes.

A relative size of one blank space 404 with respect to an adjacent electrode 402 may be described as follows. A first distance 414 (FIG. 4A) is defined as a distance between a first point 416 on a first outer edge of an electrode (e.g., 402E) and a second point 418 on a second outer edge of the electrode (e.g., 402E), with the first and second points 416/418 each being the same distance 420 from the centroid 440 of the array. A second distance 422 is defined as a distance between the first point 416 and a third point 424 on an adjacent outer edge of a second electrode (e.g., 402D), the adjacent outer edge of the second electrode and the first outer edge being located adjacent each other without any electrodes between them. The first and third points 416/424 are also each the same distance 420 from the centroid 440. The second distance 422 may be at least 80% of the length of the first distance 414. In some embodiments, the second distance 422 may be greater than or equal to the first distance 414. That way, the transducer apparatus 400 may provide sufficient space surrounding a portion of the subject's skin that has been previously exposed to an electrode element.

As shown with reference to electrodes 402A and 402F (FIG. 4A), when a bisector 430 is drawn between an outer edge 408 of the electrode 402A and the adjacent outer edge of the electrode 402F, a distance 432 from the outer edge 408 of the electrode 402A to the bisector 430 measured in a direction perpendicular to the bisector 430 equals a distance 434 from the adjacent outer edge to the bisector 430 measured in the direction perpendicular to the bisector 430, along the length of the two outer edges. That is, the outer edges of two adjacent electrodes 402 may have a constant rate of change with respect to their bisector.

A relative shape of one blank space 404 (e.g., 404C, FIG. 4A) with respect to an adjacent electrode 402 (e.g., 402C) may be described as follows. A first angle 426 greater than 0° is formed between a first edge and a second edge of the electrode element (e.g., 402C), the first angle 426 facing exterior to the array. A second angle 428 is formed between the first edge of the electrode element (e.g., 402C) and an adjacent edge of an adjacent electrode element (e.g., 402D), the second angle 428 facing exterior to the array. The value of the second angle 428 may be at least 80% of the value of the first angle 426. In some embodiments, the second angle 428 may be greater than or equal to the first angle 426. That way, the transducer apparatus 400 may provide sufficient space surrounding a portion of the subject's skin that has been previously exposed to an electrode element.

Figure 4C:
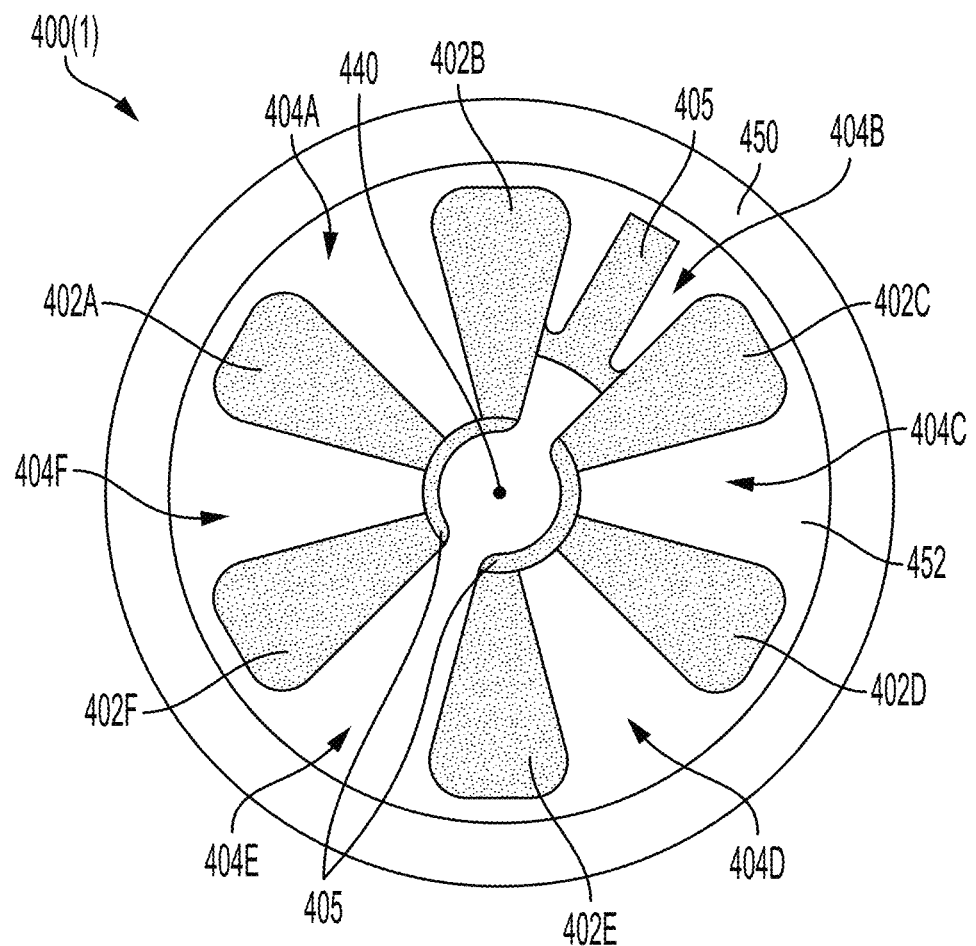
FIG. 4C depicts an example transducer apparatus having an anisotropic material layer and the electrode array layout of FIGS. 4A and 4B.

FIG. 4C depicts another example transducer apparatus 400(1). The transducer apparatus 400(1) uses the same relative positioning of the electrodes 402A-F described above with reference to FIGS. 4A and 4B. As shown, the electrodes 402A-F may be disposed on a substrate layer 450, similar to the substrates (304A, 304C, and 304E) described above with reference to FIGS. 3A, 3C, 3E, and 3F. In particular, substrate layer 450 may be an overlay bandage including an adhesive layer on the skin-facing side of the bandage. In addition, the transducer apparatus 400(1) of FIG. 4C includes an anisotropic material layer 452 directly or indirectly electrically coupled to the array of electrodes and located on a side of the face of the array configured to face the subject's body. The anisotropic material layer 452 may take any of the forms and include any of the features described above with reference to the anisotropic material layer 310E of FIGS. 3E and 3F. The anisotropic material layer 452 may be disposed over the array of electrodes such that the anisotropic material layer 452 covers the electrode elements 402A-F and the at least one blank space 404 (e.g., void space) in the array. As illustrated, the anisotropic material layer 452 may be disposed over the array of electrodes to cover the electrode elements 402A-F and every blank space 404A-F in the array. The anisotropic material layer 452, as shown, may not extend radially outward all the way to the edge of the substrate layer 450. When the transducer apparatus 400(1) of FIG. 4C is rotated from the first rotation position (e.g., as shown in FIG. 4A) to the second rotation position (e.g., as shown in FIG. 4B), the anisotropic material layer 452 will cover an area of the subject's body that was previously covered by at least a portion of an electrode 402.

Although the layout of the array of electrode elements 402A-F (in FIG. 4C) is the same as the layout of the array in FIGS. 4A and 4B, a similar arrangement of the anisotropic material layer 452 with respect to electrode elements/blank spaces may be used in embodiments having other numbers, shapes, sizes, and/or arrangements of electrode elements, e.g., as described with reference to any of FIGS. 5B and 6D-8 below. In particular, the anisotropic material layer 452 may cover both electrode elements and the space(s) therebetween. The anisotropic material layer 452 spreads heat and/or current therethrough, allowing the current to be increased (thereby increasing the therapeutic effect of the TTFields treatment) without exceeding a safety temperature threshold at any point on the subject's skin. In the event that current through the electrode elements causes hot spots or skin irritation to occur, the transducer may be rotated to prevent or reduce skin irritation.

FIGS. 5A, 5B, 6A, 6B, 6C, 6D, 6E, 6F, and 6G depict other example transducer apparatuses 500, 500(1), 600, 600(1), 600(2), 600(3), 600(4), 600(5), and 600(6), respectively. The transducer apparatuses 500, 600, 600(1), and 600(2) of FIGS. 5A and 6A-6C may include a similarly shaped array of electrodes 502A-F (i.e., 502), 602A-F (i.e., 602), 602A(1)-F(1) (i.e., 602(1)), and 602A(2)-F(2) (i.e., 602(2)) as the array of FIG. 4A. The transducer apparatus 500(1) of FIG. 5B may include a different array of electrodes (e.g., as shown, having four electrodes instead of six) 502A(1)-502D(1) (i.e., 502(1)) than the arrays of FIGS. 5A and 6A-6C, although, in other embodiments, six electrodes or other number of electrodes are similarly contemplated. Transducer arrays 600(3), 600(4), 600(5), and 600(6) also include a different array of electrodes, having either 4 electrodes (600(3), 600(4), 600(5)) or 3 electrodes (600(6)).

Figure 5A:
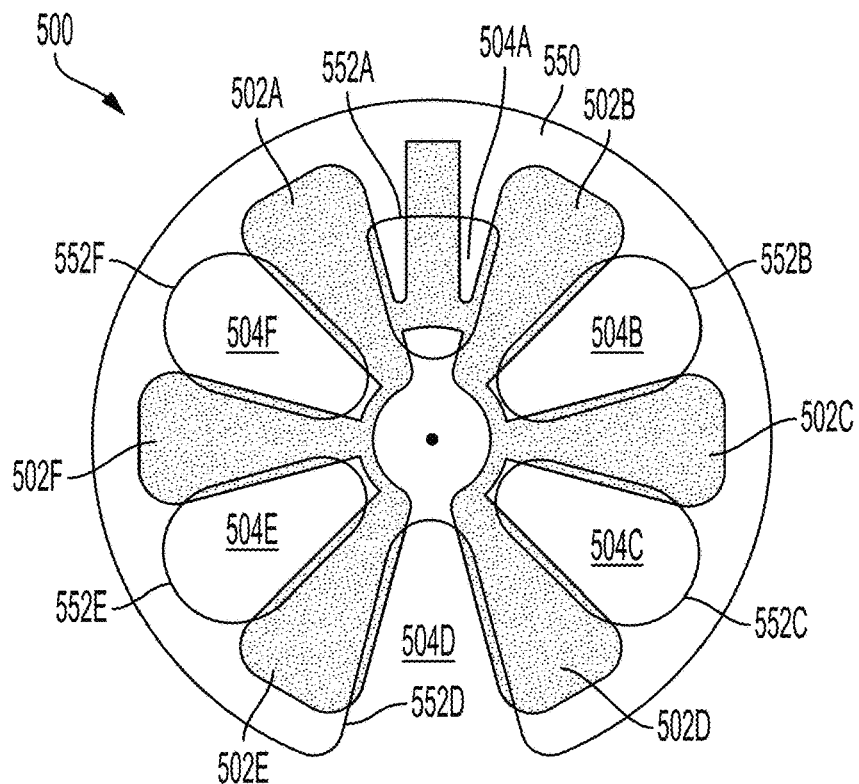
FIG. 5A depicts an example of an adhesive layer connected to an electrode array.
Figure 5B:
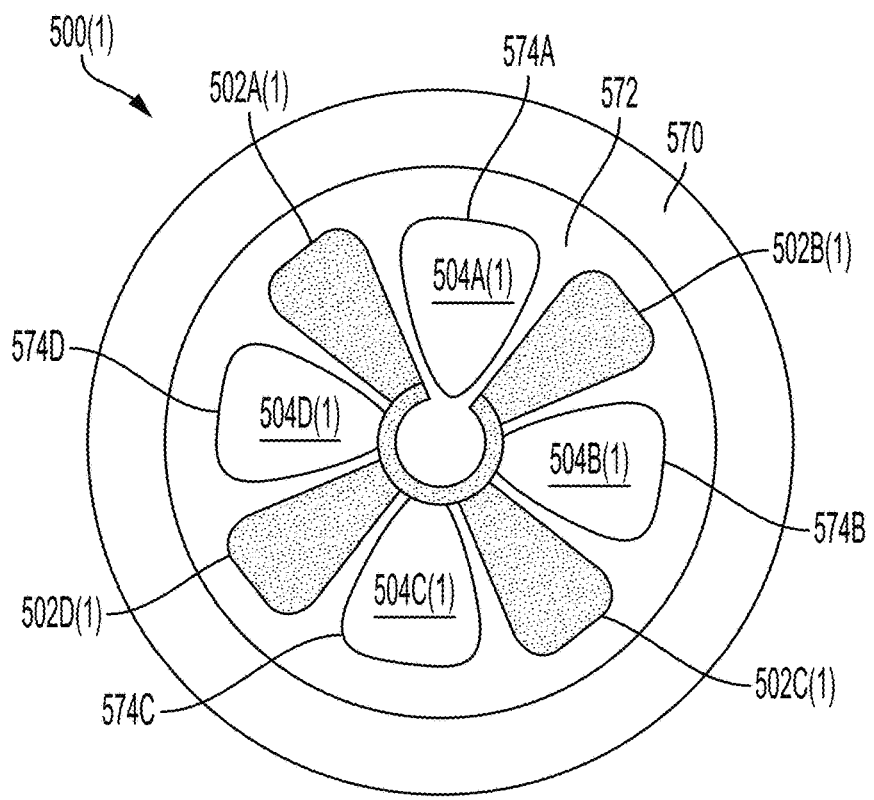
FIG. 5B depicts an example transducer apparatus having an anisotropic material layer.
Figure 6A:
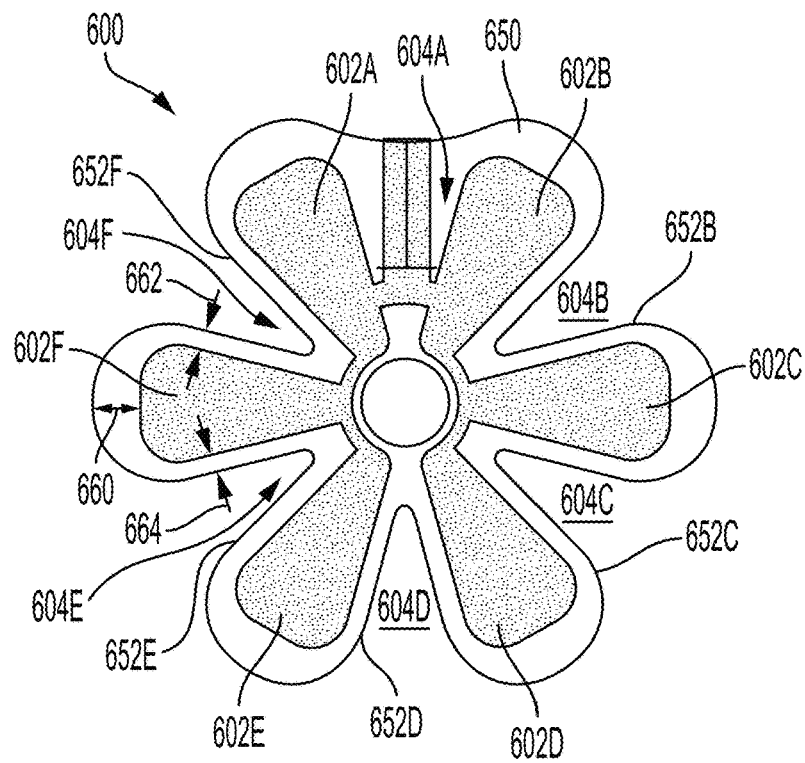
FIG. 6A depicts another example of an adhesive layer connected to an electrode array.
Figure 6B:
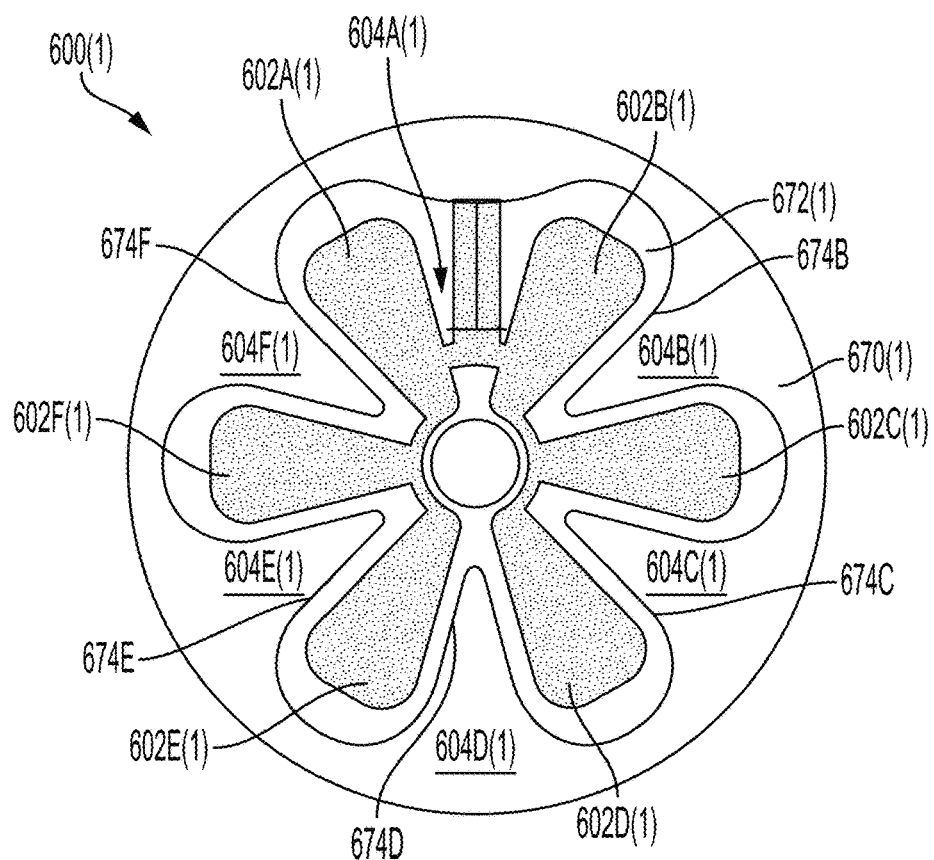
FIGS. 6B-6G depict examples of transducer apparatuses each having an anisotropic material layer.
Figure 6C:
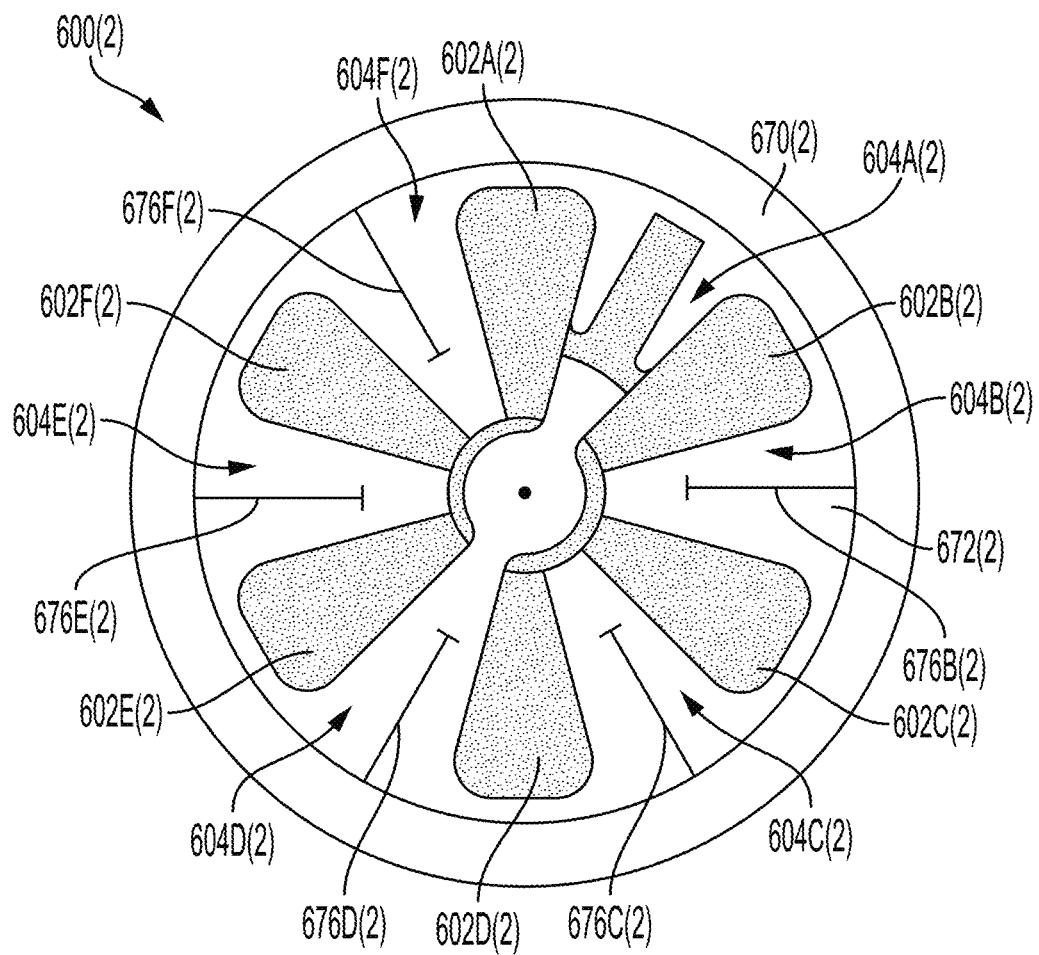

In FIGS. 5A and 6A, the transducer apparatus (500, 600) may include a substrate layer (550, 650) in the form of an adhesive layer, or overlay (tape) bandage with an adhesive layer, and an array of electrodes (502, 602) on the substrate layer. In FIGS. 5B, 6B, and 6C, the transducer apparatus (500(1), 600(1), 600(2)) includes a substrate layer (570, 670(1), 670(2)), an array of electrodes (502(1), 602(1), 602(2)) on the substrate layer (570, 670(1), 670(2)), and an anisotropic material layer (572, 672(1), 672(2)) directly or indirectly electrically coupled to the array of electrodes (502(1), 602(1), 602(2)) and located on a side of the array configured to face the subject's body (e.g., a side of the array opposite to that of the substrate layer (570, 670(1), 670(2)). In each of FIGS. 5A-6C and 6F-6G, the transducer apparatus (500, 500(1), 600, 600(1), 600(2), 600(5) 600(6)) includes the array of electrodes (502A-F, 502A(1)-D(1), 602A-F, 602A(1)-F(1), 602A(2)-F(2), 602A(5)-D(5), 602A(6)-C(6)) with spaces (504A-F, 504A(1)-D(1), 604A-F, 604A(1)-F(1), 604A(2)-F(2), 604A(5)-D(5), 604A(6)-C(6)) located therebetween.

The arrays shown in FIGS. 5A-6C are examples, and it should be noted that any number, shape, and/or arrangement of electrodes may be present in the rotational array of the transducers. For example, similar arrangements of the anisotropic material layer with respect to electrode elements/spaces may be used in embodiments having other numbers, shapes, sizes, and/or arrangements of electrode elements (e.g., as described with reference to any of FIGS. 7A-7I below).

Turning specifically to FIGS. 5A and 6A, the substrate layer (550, 650), for example an adhesive layer (or overlay bandage with an adhesive layer), may be connected to and substantially covering (from beneath) the array of electrodes (502, 602). To further enable the skin on the subject's body to breathe while it is uncovered by an electrode element, the adhesive layer (550, 650) may include one or more adhesive layer cut-outs (552A-F, 652B-F) formed therein to leave one or more spaces (504A-F, 604B-F) between the electrodes of the array uncovered. As discussed above, the cut-outs may be cut-outs through both the overlay (tape) bandage support (not shown in FIGS. 5A and 5B) and the adhesive layer, or just through the adhesive layer (for example, leaving a non-adhesive void region).

In FIG. 5A, one or more adhesive layer cut-outs 552 may have a closed shape so that the one or more cut-outs 552 are surrounded by the adhesive layer 550. The adhesive layer 550 may extend toward the outer edges of one or more electrodes 502 (from the underside), and may or may not (as shown) cover the outer edges of the one or more electrodes 502. In FIGS. 5A and 6A, one or more adhesive layer cut-outs (552, 652) may have an open shape so that the one or more cut-outs (552, 652) define one or more concave portions along an outer edge of the adhesive layer (550, 650) (see, for example, 552D in FIG. 5A and 652B-F in FIG. 6A). The adhesive layer 650 may entirely cover the outer edges of one or more electrodes 602 (from the underside), as shown in FIG. 6A. As illustrated with respect to the electrode 602F, the adhesive layer 650 may extend beyond each of the first outer edge (e.g., by a distance 662) and the second outer edge (e.g., by a distance 664) of the electrode 602F by the same amount or by a different amount, and may extend beyond an end edge (e.g., by a distance 660) of the electrode 602F located radially away from the centroid by the same amount (as distance 662 and/or distance 664) or by a different amount. In some embodiments, the adhesive layer may extend beyond an end edge of the electrode located radially away from the centroid (e.g., distance 660) by a larger amount than an amount extending towards another electrode (such as circumferentially towards another electrode) (e.g., more than distance 662 and distance 664). This may enable the adhesive layer 650 to connect the transducer apparatus 600 to a subject's skin without covering too much of the space 604 between adjacent electrodes 602.

Turning now to FIGS. 5B and 6B, the anisotropic material layer (572, 672(1)) may be directly or indirectly electrically coupled to and substantially covering (from above) the array of electrodes (502(1), 602(1)). The phrase "substantially covering" may refer to the layer covering at least 90%, at least 95%, or at least 99%, of the surface area of the electrodes in the array. To further enable the skin on the subject's body to breathe while it is uncovered by an electrode element, the anisotropic material layer (572, 672(1)) may include one or more anisotropic material layer cut-outs (574A-D, 674A-E) (i.e., 574, 674) formed therein, located over at least one void space of the array, to leave one or more spaces (504A(1)-D(1), 604A(1)-F(1)) (i.e., 504, 604) between the electrodes of the array uncovered. Optionally, one or more void space of the array may not have a corresponding cut-out in the anisotropic material layer, for example, there may be no anisotropic material layer cut-out where there is a connector or connecting wire incoming to the electrodes of the array (see, for example, FIG. 6B); or, alternatively, there may be a smaller size cut-out in a void area containing the connector or connecting wire (for example, analogous to the adhesive layer cut-out 552A in FIG. 5A, which does not show an anisotropic material layer). The anisotropic material layer cut-outs (574, 674) may be formed through the anisotropic material layer (572, 672(1)) and, optionally, also through any other conductive layers (e.g., conductive adhesive material layer(s) 316(E) and conductive material layer 318(E) of FIGS. 3E and 3F) that are packaged with the anisotropic material layer. The anisotropic material layer cut-outs (574, 674) may or may not be formed through the substrate layer (570, 670(1)) as well. As an example, the substrate layer (570, 670(1)) covers the anisotropic material layer cut-outs (574, 674), and the anisotropic material layer cut-outs (574, 674) are aligned with non-adhesive regions of the substrate layer (570, 670(1)). When the transducer apparatus (500(1), 600(1)) is rotated from a first position to a second position, the anisotropic material layer (572, 672(1)) does not cover at least part of an area of the subject's body that was previously covered in the first position by at least a portion of an electrode (502(1), 602(1)) (because this region of the anisotropic material layer in the second position presents a cut-out region instead).

In some embodiments, the anisotropic material layer cut-out areas (574, 674) may provide relief regions as discussed herein. For example, the anisotropic material layer cut out areas (574, 674) may contain medication regions comprising a medication substrate and a topical medication integrated therein or thereon used to administer a topical medication to an area of the subject's skin, or the anisotropic material layer cut out areas (574, 674) may contain non-adhesive regions comprising a medication substrate capable of receiving, absorbing, and/or holding a topical medication applied thereto. For example, the overlay bandage may include regions on the skin-facing side that are covered with a gauze or other medication substrate (with or without medication), which regions align with the pattern of the anisotropic material layer cut-outs (574, 674) when the transducer array is constructed; or the overlay bandage may already be constructed with the electrode array and the anisotropic material layer, and gauze patches or other medication substrates (with or without medication) could be attached to the adhesive areas showing through the anisotropic material layer cut-out areas (574, 674). Where medication substrates without a medication are used in the anisotropic material layer cut-out areas (574, 674), the medication could be added by the patient or helper/caregiver between periods of treatment, for example, just prior to the shifting (e.g., rotation or translation) of the transducer array.

In an alternative embodiment, the cut-out regions described herein may include only the front-facing conductive adhesive material (e.g., conductive adhesive material 316E disposed on the front facing side of the anisotropic material layer 310E in FIG. 3F), and does not include the anisotropic material layer.

In FIG. 5B, one or more anisotropic material layer cut-outs 574 may have a closed shape so that the one or more cut-outs 574 are surrounded by the anisotropic material layer 572. The anisotropic material layer 572 may extend toward and cover all outer edges of the one or more electrodes 502(1), as shown. In FIG. 6B, one or more anisotropic material layer cut-outs 674 may have an open shape so that the one or more anisotropic material layer cut-outs 674 define one or more concave portions along an outer edge of the anisotropic material layer 672(1). The anisotropic material layer 672(1) may entirely cover the outer edges of one or more electrodes 602(1) (from above), as shown in FIG. 6B. In the embodiments of FIGS. 5B and 6B, the substrate layer (570, 670(1)) may be substantially rounded in shape, as shown (e.g., circular, oval, etc.) or contoured to match the shape of the anisotropic material layer (572, 672(1)) (e.g., contoured to match a shape of the outer edge of the anisotropic material layer (572, 672(1)) at one or more concave portions along the outer edge of the anisotropic material layer (572, 672(1))). In some embodiments, the substrate layer (570, 670(1)) may be contoured with slits extending into gaps (e.g., void spaces) between electrodes (502(1), 602(1)). The latter embodiments may allow for increased flexibility for adhering to non-flat (e.g., curved) surfaces, such as the subject's head.

Turning now to FIG. 6C, the anisotropic material layer 672(2) may be directly or indirectly electrically coupled to and substantially covering (from above) the array of electrodes 602(2), and the anisotropic material layer 672(2) may include at least one cut or slit formed therein. In FIG. 6C, for example, the anisotropic material layer 672(2) has five cuts or slits 676B(2)-676F(2) (i.e., 676(2)) formed therein. The cut(s) or slit(s) 676(2) may be formed through a full thickness of the anisotropic material layer 672(2). The cut(s) or slit(s) 676(2) may extend from an outer edge of the anisotropic material layer 672(2) toward a center portion of the anisotropic material layer 672(2). The cut(s) or slit(s) 676(2) may extend into gaps (e.g., void spaces) 604A(2)-604F(2) (i.e., 604(2)) between electrodes 602A(2)-602F(2) (i.e., 602 (2)). The cut(s) or slit(s) 676(2) allow the anisotropic material layer 672(2) to separate enough to provide some flexibility for stretching, twisting, or other movement of the subject's body when the transducer apparatus 600(2) is attached to the subject's body. The perimeter of the anisotropic material layer may be contoured to follow the perimeter of the electrodes, as shown for the anisotropic material layer 672(1) in FIG. 6B. The substrate layer 670(2) may be similarly contoured, optionally with cuts or slits extending into the gaps (e.g., void spaces) 604(2) between electrodes 602(2), and such cuts or slits in the substrate layer 670(2) may be at least partially coincident with cuts or slits in the anisotropic material layer 672(2). In other embodiments, such as shown in FIG. 6C, the substrate layer 670(2) is flexible and does not include cuts or slits.

Figure 6D:
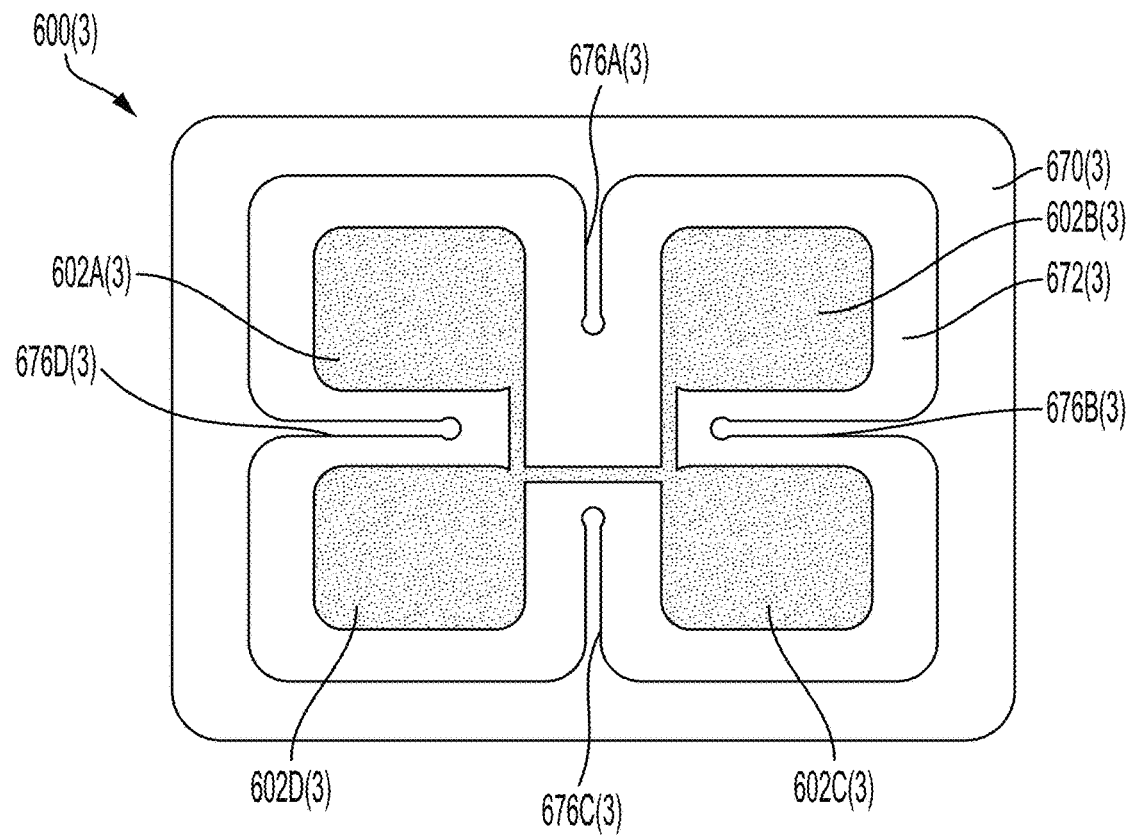
Figure 6E:
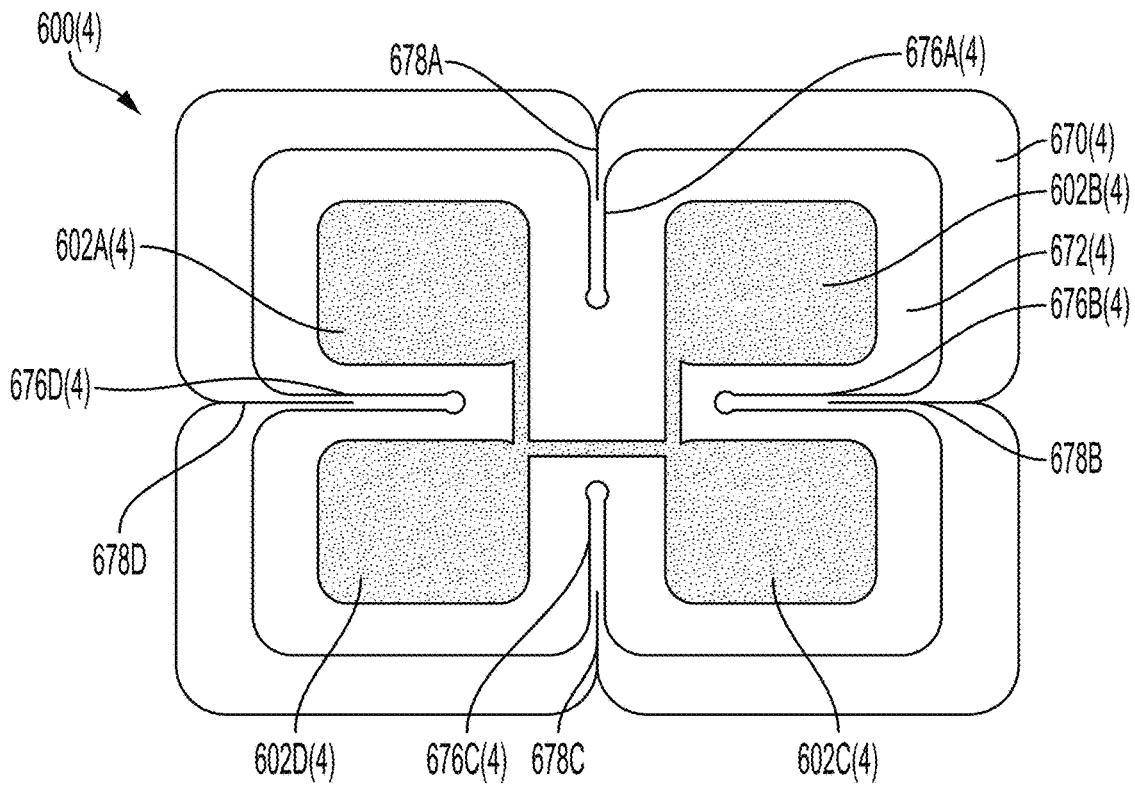

FIGS. 6D and 6E depict other example transducer apparatuses 600(3) and 600(4), respectively. The transducer apparatuses 600(3) and 600(4) each include a substrate layer (670(3), 670(4)) and an array of electrodes (602A(3)-602D (3), 602A(4)-602D(4)) (i.e., 602(3), 602(4) disposed on the substrate layer (670(3), 670(4)). The array is configured to be positioned over the subject's body with a front face of the array facing the subject's body. The transducer apparatuses 600(3) and 600(4) also include an anisotropic material layer (672(3), 672(4)) directly or indirectly electrically coupled to the array of electrodes (602(3), 602(4)) and located on a side of the array opposite the substrate layer (670(3), 670(4)). The anisotropic material layer (672(3), 672(4)) may have at least one cut or slit (676A(3)-676D(3), 676A(4)-676D(4)) (i.e., 676(3), 676(4)) formed through a full thickness of the anisotropic material layer (672(3), 672(4)). As shown, each cut or slit (676(3), 676(4)) may extend from an outer edge of the anisotropic material layer (672(3), 672(4)) toward a center portion of the anisotropic material layer (672(3), 672(4)) when viewed in a direction perpendicular to the face of the array. The cut(s) or slit(s) (676(3), 676(4)) allow the anisotropic material layer (672(3), 672(4)) to separate enough to provide some flexibility for stretching, twisting, or other movement of the subject's body when the transducer apparatus (600(3), 600(4)) is attached to the subject's body. In the transducer apparatus 600(3) of FIG. 6D, the substrate layer 670(3) does not include any cuts or slits. In the transducer apparatus 600(4) of FIG. 6E, the substrate layer 670(4) has at least one cut or slit (678A-678D) (i.e., 678) formed through a full thickness of the substrate layer 670(4), the cut or slit 678 extending from an outer edge of the substrate layer 670(4) toward a center portion of the substrate layer 670(4) when viewed in the direction perpendicular to the face of the array. As illustrated, the cuts or slits 678 formed in the substrate layer 670(4) may be at least partially coincident with the cuts or slits 676(4) formed in the anisotropic material layer 672(4). The transducer apparatuses 600(3) and 600(4) of FIGS. 6D and 6E have increased flexibility compared to transducers that do not feature such cuts or slits formed in the anisotropic material layer or substrate layer. The cuts or slits (in the anisotropic material layer, or the substrate layer, or both—in the latter case, coincident or otherwise) may be applied to transducers having any desired shape, number, and arrangement of electrodes, not just those configured to provide relief areas in response to rotational shifting (e.g., FIGS. 4A-6C, and 7A-7I) or translational shifting (e.g., FIG. 8).

Figure 6F:
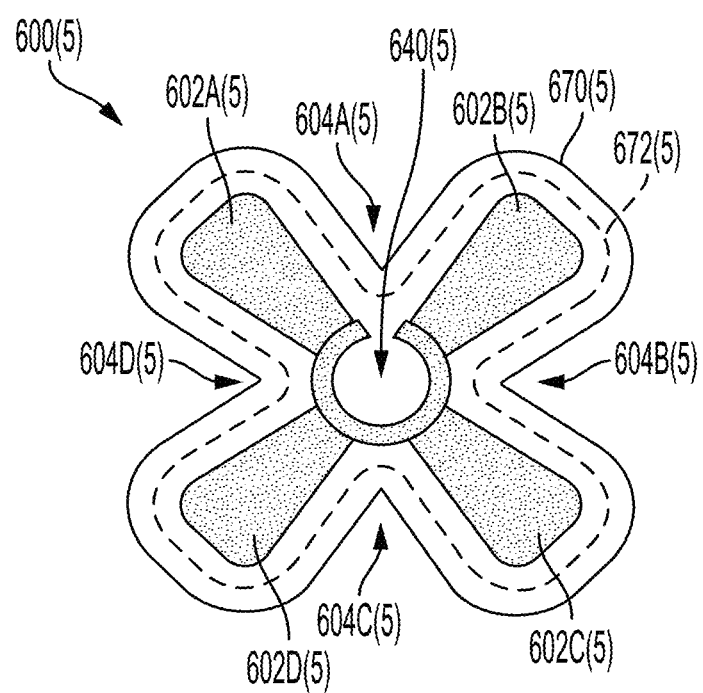
Figure 6G:
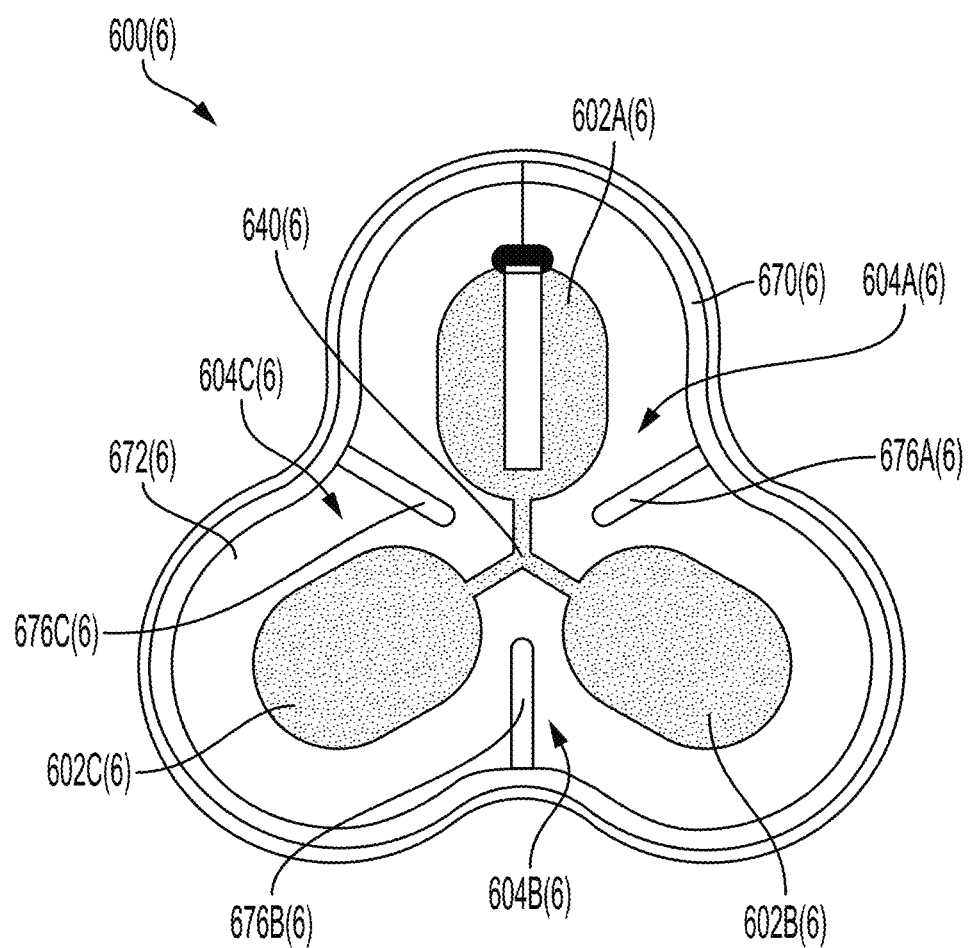

FIGS. 6F and 6G depict other example transducer apparatuses 600(5) and 600(6), respectively. The transducer apparatuses 600(5) and 600(6) each include an array of electrodes 602A(5)-602D(5), 602A(6)-602C(6) (i.e. 602(5), 602(6)) disposed on a substrate layer 670(5), 670(6), optionally paired with an anisotropic material layer 672(5), 672(6), where it may either not be present or may be coincident with the areal trace of the electrodes. The anisotropic material layer 672(5), 672(6) may extend beyond the periphery of the areal footprint of the electrodes and may or may not be contoured to mirror the shape of the outer periphery of the areal trace of the electrons. In some embodiments, a front face of the array of electrodes 602(5), 602(6) faces a subject's body, and the anisotropic material layer 672(5), 672(6) covers the front face of the array of electrodes 602(5), 602(6) and extends (radially) outwardly from each electrode 602(5), 602(6) to at least partially cover each void space 604A(5)-604D(5), 604A(6)-604C(6) (i.e., 604(5), 604 (6)) in the array. In some embodiments, the anisotropic material layer 672(5), 672(6) may be composed of graphite (such as, for example, pyrolytic graphite). In some embodiments, the substrate layer 670(5), 670(6) may cover the array of electrodes 602(5), 602(6) and the anisotropic material layer 672(5), 672(6) and may extend (radially) outwardly from the combined areal footprint of each electrode 602(5), 602(6) and associated anisotropic material layer to at least partially cover each void space 604(5), 604(6) in the array (covering more than the areal footprint of the anisotropic material layer 672(5), 672(6)). In some embodiments, the substrate layer 670(5), 670(6) completely covers each void space 604(5), 604(6).

In some embodiments (such as in FIG. 6F), the apparatus 600(5) includes at least four electrodes 602(5), and in some embodiments (such as in FIG. 6G), the apparatus 600(6) includes at least three electrodes 602(6). In some embodiments, the array of electrodes 602(5), 602(6) has point symmetry. Transducer apparatus 600(5), 600(6) may include an array of electrode elements 602(5), 602(6) arranged around a centroid 640(5), 640(6). For example (such as in FIG. 6F), the array of electrodes may include four electrodes having point symmetry (C4 symmetry) about the centroid 640(5). For example (such as in FIG. 6G), the array of electrodes may include three electrodes having point symmetry (C3 symmetry) about the centroid 640(6). Each electrode may be substantially similar in size and shape. In some embodiments, the substrate layer 670(5), 670(6) may cover all of the electrodes 602(5), 602(6) and all of the void spaces 604(5), 604(6) between the electrodes 602(5), 602(6). In some embodiments, the substrate layer 670(5), 670(6) paired to the apparatus 600(5), 600(6) includes one or more cutouts coincident with at least a portion of the void spaces 604(5), 604(6) between at least one of the pairs of electrodes 602(5), 602(6). The cutouts may have an open shape so that the one or more cutouts define one or more concave portions along an outer edge of the substrate layer 670(5), 670(6) when viewed from a direction perpendicular to the face of the array. For the embodiments of FIG. 6F and FIG. 6G, a 45° rotation or a 60° rotation, respectively, of the existing electrode positions about the centroid 640(5), 640(6) positions each void space over the former existing electrode position, thereby providing relief to the areas of skin that may have experienced skin irritation from the electrodes. Furthermore, the substrate layer 670(5), 670(6) provides flexibility to the transducer array apparatus and allows the array to accommodate movements of the skin due to movements of the torso of the subject. In some embodiments, and as shown in FIG. 6G, cuts or slits 676A(6)-676C(6) (i.e. 676(6)) in the anisotropic material layer 672(6) and/or the substrate layer 670(6) as described elsewhere herein may provide additional flexibility of the substrate layer 670(6) and/or the anisotropic material layer 672(6) to accommodate movements of the skin due to movements of the torso of the subject. Although shown for 4 electrodes and arrays with C4 rotational symmetry in FIG. 6F and for 3 electrodes and arrays with C3 rotational symmetry in FIG. 6G, similar constructs with other rotational symmetry are readily envisioned (e.g., with 2, 5, 6, or more electrodes), as well as other electrode arrays spaced and arranged to allow for a translational shift of the electrode array.

Other arrangements of the array of electrodes may enable rotational shifting to minimize, reduce, prevent, soothe, heal, and/or treat skin irritation during TTFields treatment. Various examples of such electrode arrays are shown in FIGS. 7A-7I. The present disclosure is not limited to the arrangements of electrode elements and relief regions (e.g., void regions or medication regions) depicted in these examples, as many others may be possible without departing from the scope of the claims.

FIGS. 7A-7I provide further examples of arrays of electrodes that may be suitable for use in the transducer apparatuses and methods of use described herein. Although, for purposes of clarity, FIGS. 7A-7I do not show the anisotropic material layer and other features of the invention described herein, it is understood that the arrays of electrodes shown here may be combined with the anisotropic material layer and associated features as described herein.

Each of FIGS. 7A-7I illustrates an array (700A, 700B, 700C, 700D, 700E, 700F, 700G, 700H, 700I) of electrodes comprising multiple electrode elements (702A, 702B, 702C, 702D, 702E, 702F, 702G, 702H, 702I) and one or more blank spaces where no electrode elements are present. Each blank space may be or may include one or more relief regions (704A, 704B, 704C, 704D, 704E, 704F, 704G, 704H, 704I).

The term "relief regions" 704 (and 804 of FIG. 8) as used herein refers to either 1) void regions of the transducer apparatus that are fully uncovered or fully uncovered other than the transducer substrate and/or an anisotropic material layer (with or without conductive adhesive layer(s) and/or a conductive layer), 2) non-adhesive regions comprising a medication substrate capable of receiving, absorbing, or holding a topical medication applied thereto, or 3) medication regions of the transducer apparatus comprising a medication substrate and a topical medication integrated therein or thereon used to administer a topical medication to an area of the subject's skin. These relief regions 704 may optionally, have no exposed adhesive present.

The electrode elements 702 are positioned in existing electrode positions (708A, 708B, 708C, 708D, 708E, 708F, 708G, 708H, 708I) arranged around a centroid (706A, 706B, 706C, 706D, 706E, 706F, 706G, 706H, 706I) of the array 700. Each of the electrode elements 702 may trace an existing electrode footprint, illustrated via solid outlines in FIGS. 7A-7I. The existing electrode footprints are areal footprints of the existing electrode positions 708. The one or more blank spaces may define potential electrode positions (710A, 710B, 710C, 710D, 710E, 710F, 710G, 710H, 710I), which are positions that might otherwise be occupied by electrode elements 702 upon certain rotations of the array 700. The potential electrode positions 710 are arranged around the centroid 706 of the array, and each potential electrode position 710 traces a potential electrode footprint, illustrated via dashed outlines in FIGS. 7A-7I. The potential electrode footprints are areal footprints of the potential electrode positions 710.

In some embodiments, the relief regions 704 of the array 700 occupy at least the potential electrode positions 710. As an example, the relief regions 704 occupy only the areal footprints defined by the potential electrode positions 710. In another example, the one or more relief regions 704 of an array 700 may occupy greater portion(s) of the blank space(s) between adjacent electrodes 702 than what is defined by the potential electrode positions 710.

In each of FIGS. 7A-7I, at least one relief region 704 in the array 700 is capable of enclosing an areal footprint equivalent to at least 40%, or at least 50%, of the areal footprint of at least one electrode 702, and superimposable on at least 40%, or at least 50%, of the existing electrode position 708 by rotation of the array 700 around the centroid 706. For example, in FIG. 7D, one such relief region 704D(2) is capable of enclosing and superimposable via rotation upon at least 40% of the areal footprint (708D(1)) of the larger electrode element 702D(1). In some embodiments, the at least one relief region 704 in the array is capable of enclosing an areal footprint equivalent to at least 95% (e.g., 100%) of an areal footprint of at least one existing electrode position 708, and superimposable on at least 95% (e.g., 100%) of the existing electrode position 708 by rotation of the array around the centroid 706. For example, in FIG. 7D, a relief region 704D(2) is capable of enclosing and superimposable via rotation upon the entire areal footprint (708D(2)) of the smaller electrode element 702D(2).

In FIGS. 7A-7E, 7H, and 7I, at least one electrode element 702 extends radially outward away from the centroid 706. In FIGS. 7A, 7E, 7H, and 7I, a sum total of the areal footprints for every relief region 704 in the array is approximately 50% of a sum total of the combined areal footprints for every relief region 704 and every existing electrode position 708 of the array. That is, the relief regions 704 take up approximately the same total area as the electrode elements 702 in the transducer apparatus. As shown in each of FIGS. 7A-7I, the sum total of the areal footprints for every relief region 704 in the array may be equivalent to at least 20% of a sum total of the combined areal footprints for every relief region 704 and every existing electrode position 708 of the array, such that the relief regions 704 take up at least one fourth the amount of area as the electrode elements 702 in total.

In some embodiments, each potential electrode footprint (710) has an identical shape, area, orientation with respect to the centroid 706, and distance from the centroid 706, as that of one or more existing electrode footprints (708). In addition, each potential electrode footprint (710) is in rotational coincidence about the centroid 706 with one or more existing electrode footprints (708) such that a rotational shift of the electrode array 700 about the centroid 706 may position at least one potential electrode position 710 to be coincident upon an existing electrode position 708. This rotation provides a resting state (or application of a topical medication) for an area of skin beneath at least one electrode after the rotation. In some embodiments, the total area occupied by potential electrode positions 710 may be no greater than 50% of the sum of the total areas of the potential electrode positions 710 and existing electrode positions 708.

Figure 7B:
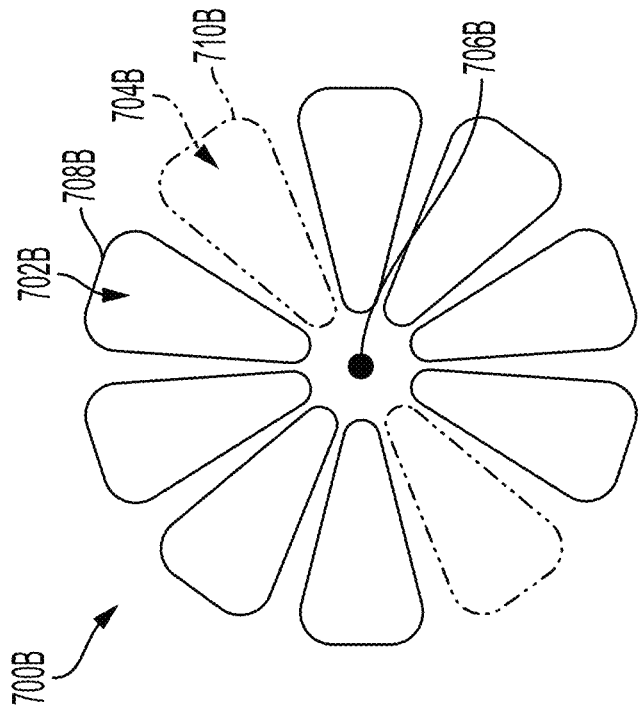
FIGS. 7A-7I depict example layouts of arrays of electrode elements and relief regions.
Figure 7A:
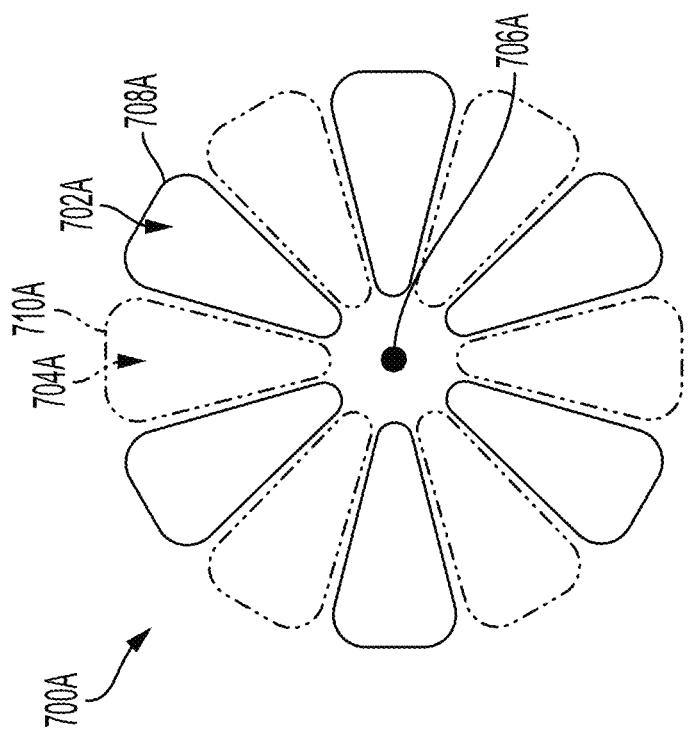

In some embodiments, the combined distribution of potential electrode positions 710 and existing electrode positions 708 in the arrays 700 may exhibit Cx symmetry with respect to rotation about the centroid 706, where x is an integer and the potential electrode footprints are considered to be identical to the existing electrode footprints in determining rotational symmetry of the combined electrode positions 708 and 710. For example, with respect to the combined distribution of potential electrode positions and existing electrode positions, FIG. 7A depicts an array 700A having C12 symmetry, as there are twelve rotationally symmetrical positions about the centroid 706A at which the combined electrode positions 708A/710A may be located; the array 700B of FIG. 7B has C10 symmetry; the array 700C of FIG. 7C has C9 symmetry; the arrays 700D, 700H, and 700I of FIGS. 7D, 7H, and 7I have C2 symmetry; the arrays 700E and 700F of FIGS. 7E and 7F have C8 symmetry; and the array 700G of FIG. 7G has C4 symmetry.

In addition, the rotational symmetry of the existing electrode positions 708 with respect to rotation about the centroid 706 is either Cx', or no rotational symmetry, wherein x' is an integer. For example, FIG. 7A depicts an array 700A having an x' value of six, as there are six rotationally symmetrical existing electrode positions 708. In the examples of FIG. 7A and 7E, the value of x is equivalent to the value of 2x'. In FIG. 7B, the value of x is equivalent to 5x'. In FIG. 7C, the value of x is equivalent to 3x'. In FIG. 7F, the value of x is equivalent to 4x'.

Productive rotations of the array are given by rotations of 360/x degrees and integer multiples thereof except for rotations of 360/x' degrees and integer multiples thereof (which is an unproductive rotation). An "unproductive rotation" results in an equivalent array pattern with the same areas of skin covered by existing electrode positions 708, while a "productive rotation" results in at least one existing electrode position 708 being exchanged for a potential electrode position 710, thus giving the subject's skin an opportunity to recover or receive an application of medication. In some embodiments, at least one rotation about the centroid 706 results in all potential electrode positions 710 moving to be coincident with positions previously occupied by existing electrode positions 708, thereby providing in a single rotation a resting state (or application of a topical medication) for all areas of skin beneath all of the electrodes in existing electrode positions (for example, arrays 700A, 700E, 700H, 700I).

Figure 7D:
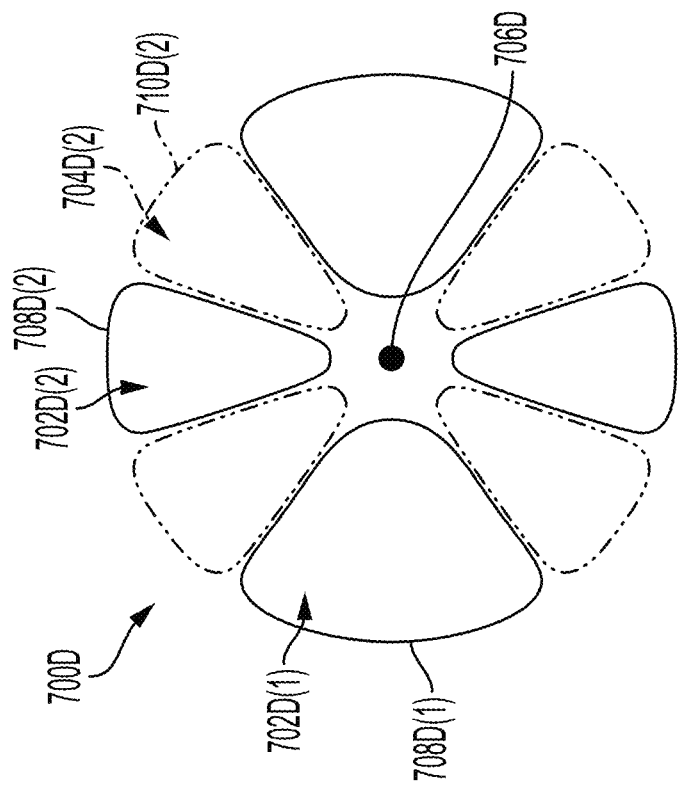
Figure 7C:
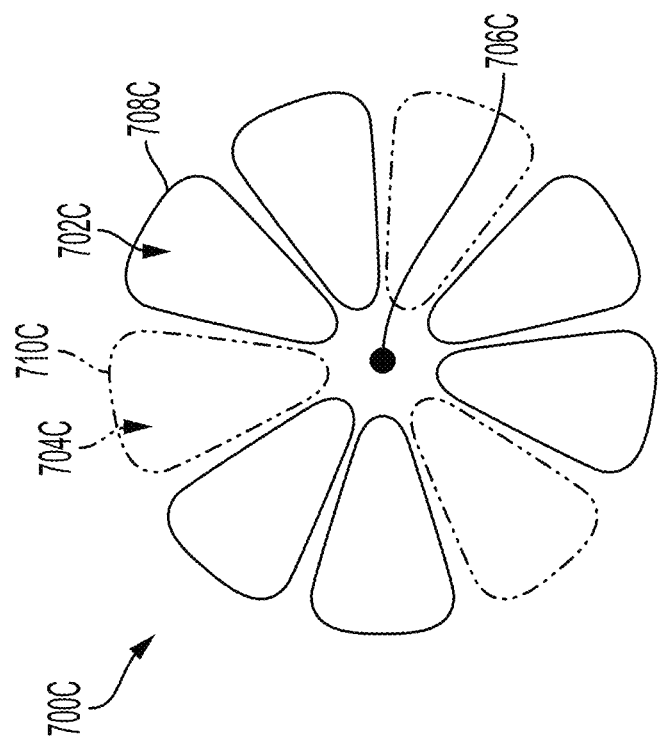
Figure 7E:
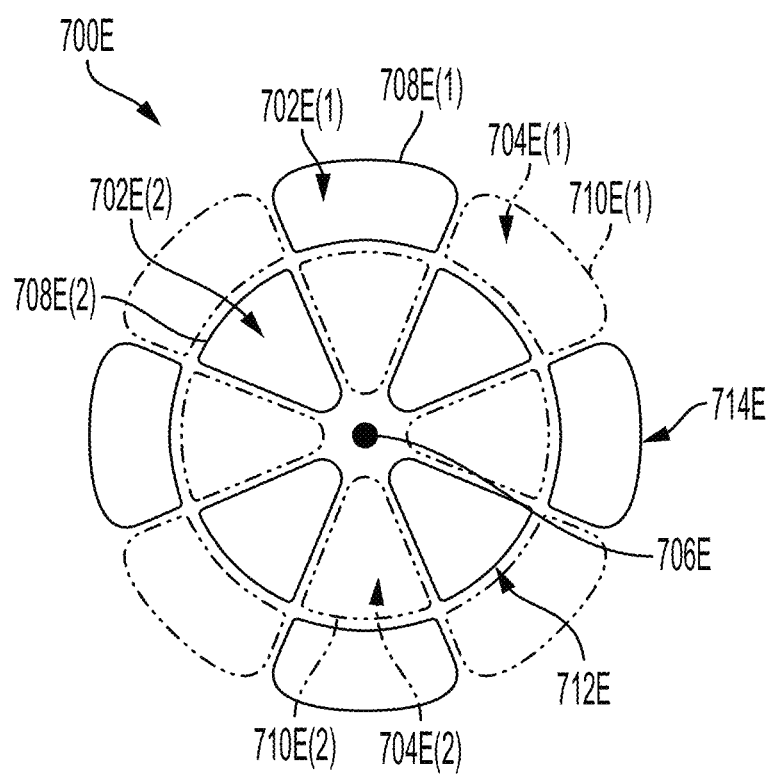

As shown in FIG. 7D, the existing electrode footprint of at least one electrode element 702D(1) of the array may have a different shape than, and an identical distance from the centroid 706 as, the potential electrode footprint of at least one potential electrode position 710. As shown in FIGS. 7D, 7E, 7G, 7H, and 7I, the existing electrode footprint of at least one electrode element (702D(1), 702E(1), 702G(1), 702H(1), 702I(1)) of the array has a different shape than the existing electrode footprint of at least one other electrode element 702D(2), 702E(2), 702G(2), 702H(2), 702I(2) of the array.

As shown in FIGS. 7E and 7F, the one or more relief regions 704 may define a first potential electrode position (710E(1), 710F(1)) located a first distance from the centroid 706 and a second potential electrode position (710E(2), 710F(2)) located a second distance from the centroid 706, the first and second distances being different from each other. In such instances, the first potential electrode position 710E(1) may be circumferentially offset from the second potential electrode position 710E(2) as in FIG. 7E, or the first potential electrode position 710F(1) may be in radial alignment with the second potential electrode position 710F(2) as in FIG. 7F. In FIG. 7E (and FIGS. 7F and 7G), the array 700E may include a first group of electrode elements 702E arranged in a first circular region 712E around the centroid 706E, and a second group of electrode elements 702E separate from the first group and arranged in a second circular region 714E concentric with the first circular region 712E.

Figure 7G:
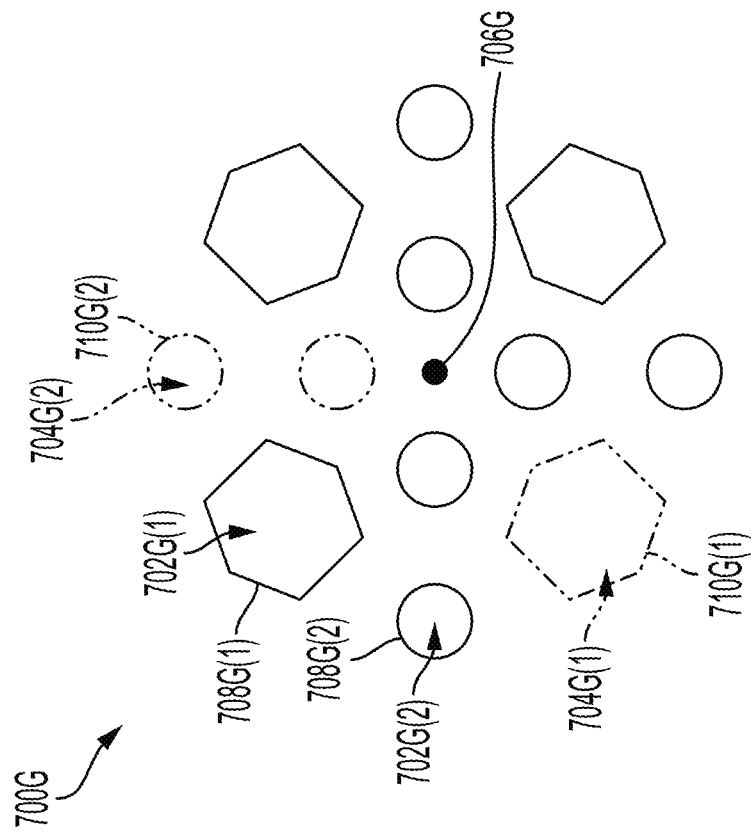
Figure 7F:
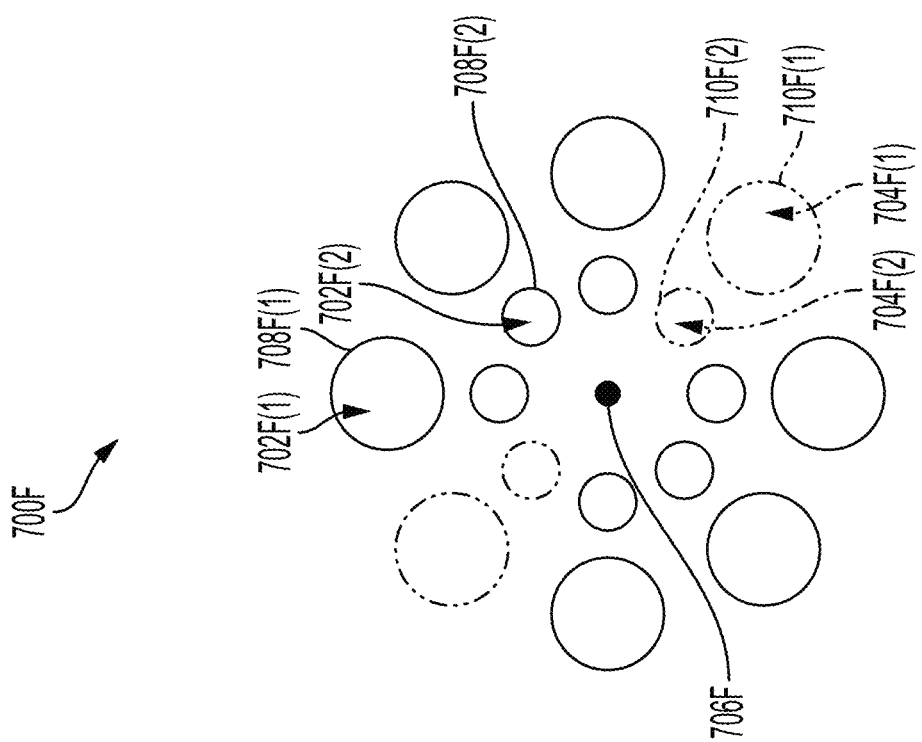
Figure 7H:
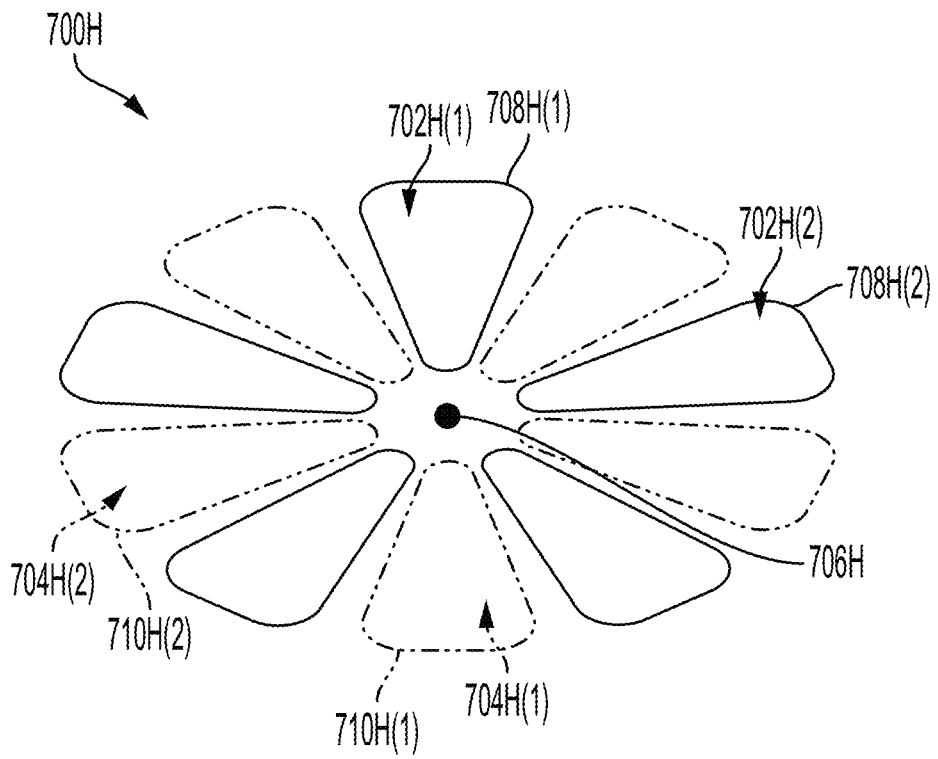
Figure 7I:
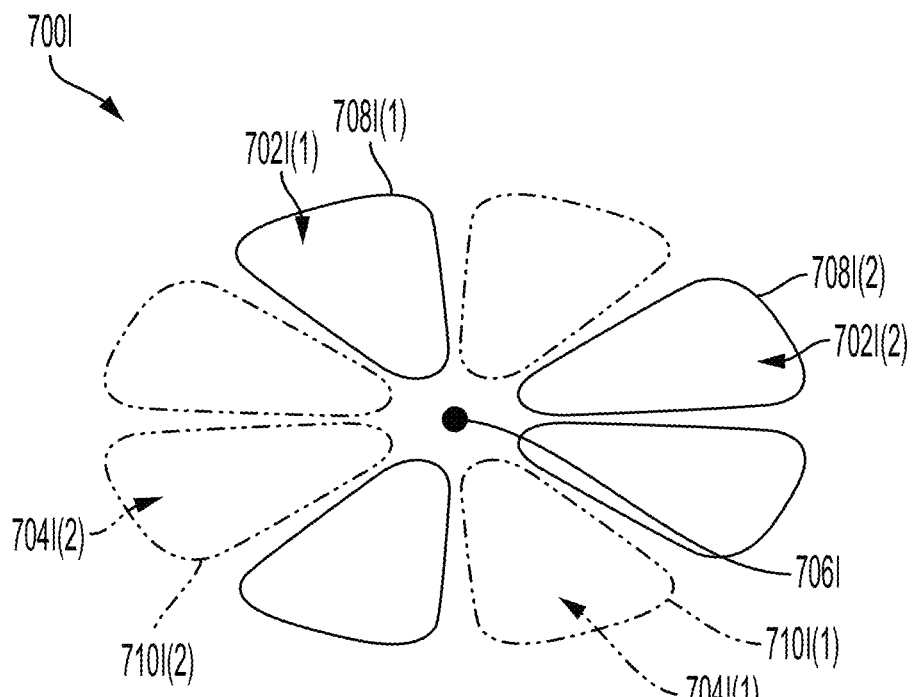

As shown in FIG. 7F, the existing electrode footprint of at least one electrode element 702F(1) of the array 700F may have a different size than the existing electrode footprint of at least one other electrode element 702F(2) of the array 700F. In such instances, the electrode element 702F(1) may have a similar shape as the different sized electrode element 702F(2), as shown (FIG. 7F), or a different shape (FIG. 7G). As shown in FIGS. 7H and 7I, the overall array 700 (700H, 700I) of electrodes may have a non-circular shape. For example, the array 700 may have an oval, ovaloid, ovoid, or elliptical shape. This may allow the array 700 to be used to induce desired TTFields while still providing rotational symmetry for shifting the electrodes with respect to the subject's skin. Both of the arrays 700H and 700I may undergo a 180° rotation about the centroid 706 (706H, 706I) and result in all potential electrode positions 710 moving to be coincident with positions previously occupied by existing electrode positions 708, thereby providing in a single rotation a resting state (or application of a topical medication) for all areas of skin beneath all of the electrodes in existing electrode positions.

FIG. 8 provides a further example of an array of electrodes that may be suitable for use in the transducer apparatuses and methods of use described herein. Although FIG. 8 does not show the anisotropic material layer and other features of the invention described herein, it is understood that the array of electrodes shown in FIG. 8 may be combined with the anisotropic material layer and associated features as described herein.

FIG. 8 depicts an example transducer apparatus 800 that may be used to apply TTFields to a subject's body. The transducer apparatus 800 may enable a simple translation of the transducer with respect to the subject's body to reposition at least one relief region 804 formed in the electrode array over an area of the subject's skin that was previously covered by an electrode element 802 (an existing electrode position). The relief regions 804A and 804B may be either void regions in the transducer apparatus 800 that are fully uncovered or fully uncovered other than the transducer substrate and/or an anisotropic material layer (with or without conductive adhesive layer(s) and/or a conductive layer); or non-adhesive regions comprising a medication substrate capable of receiving, absorbing, or holding a topical medication applied thereto; or medication regions of the transducer apparatus comprising a medication substrate and a topical medication integrated therein or thereon used to administer a topical medication to an area of the subject's skin. In some embodiments, the medication substrate may be a portion of the transducer substrate. In some embodiments, the transducer apparatus 800 may include an anisotropic material layer that covers some or all of the electrode elements 802, and that covers or does not cover the relief regions 804. For example, cut-out regions in the anisotropic material layer and/or the conductive adhesive layer and/or the conductive layer, as described earlier with respect to FIG. 5B, may be present so that the anisotropic material layer does not cover the relief regions 804 or only partially covers the relief regions 804. Each relief region 804 may be capable of enclosing an areal footprint (potential electrode footprint) equivalent to at least 40%, or at least 50%, or at least 95%, of an areal footprint of at least one of the electrode elements 802 of the transducer 800 of FIG. 8. When viewed from the direction perpendicular to the face of the array of electrodes, the electrode elements 802 are positioned in existing electrode positions 808. Each of the electrode elements 802 may trace an existing electrode footprint. The existing electrode footprints are areal footprints of the existing electrode positions 808. The relief regions 804A and 804B may define potential electrode positions, respectively, which are positions that might otherwise be occupied (i.e., potential electrode footprints) by electrode elements 802 upon certain translations of the transducer apparatus 800. As illustrated, multiple existing electrode positions 808 may be arranged in a line 830. For example, three lines 830A, 830B, and 830C of existing electrode positions 808 are shown in the transducer 800 of FIG. 8. Both relief regions 804A and 804B may be superimposable on at least 40%, or at least 50%, or at least 95%, or even 100% of the areal footprint of each of the existing electrode positions 808 arranged in an individual line (e.g., 830A, 830B, or 830C) by translation of the array with respect to the subject's body.

Figure 9:
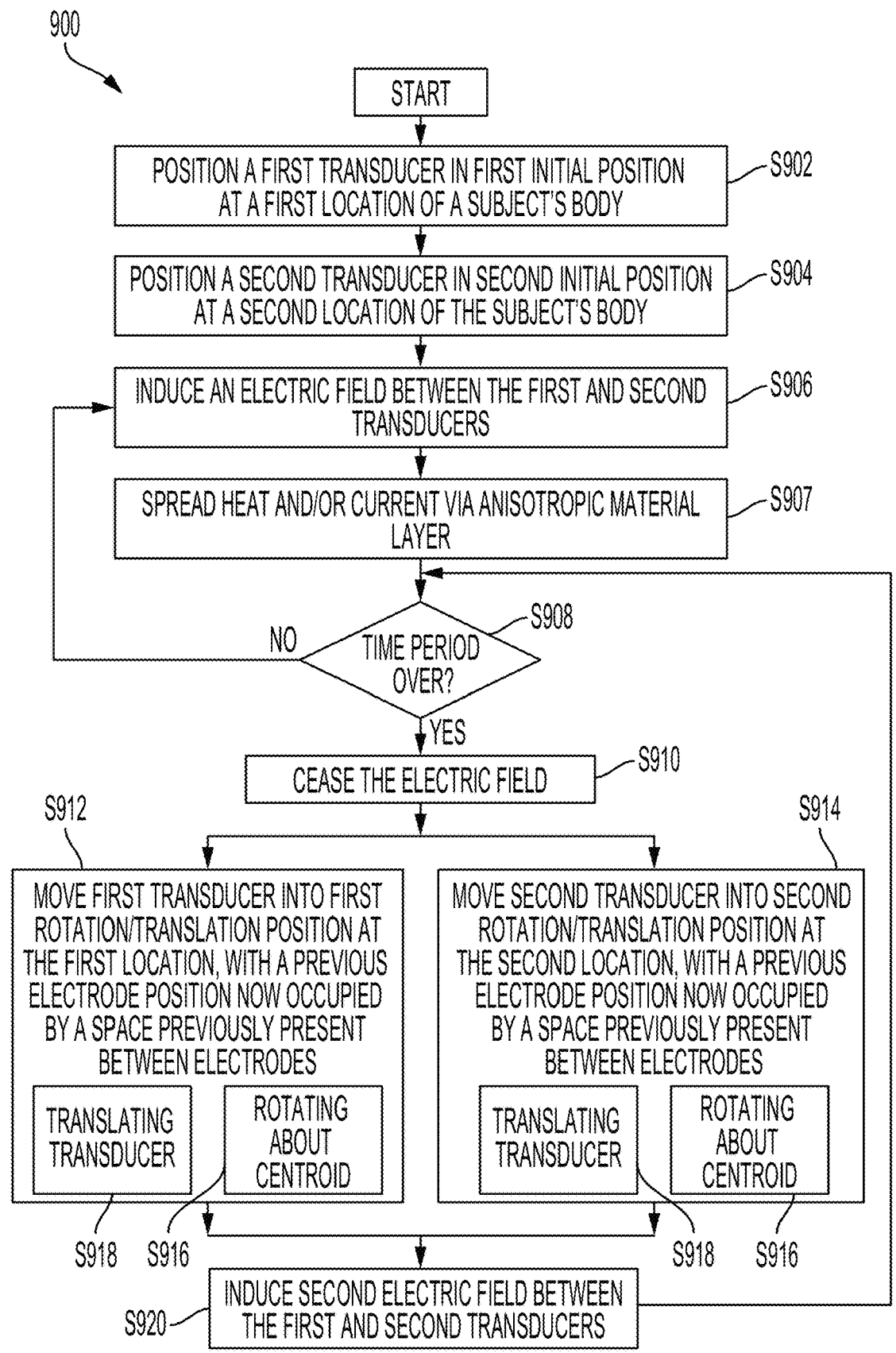
FIG. 9 is a flowchart depicting an example of applying TTFields to a subject's body.

FIG. 9 depicts an example method 900 of applying TTFields to a subject's body in accordance with the present techniques. The method 900 begins at step S902 with positioning a first transducer in a first initial position at a first location of the subject's body. The first transducer may include a plurality of electrodes in initial electrode positions and at least one void space located between adjacent electrodes (e.g., as shown in the apparatuses of FIGS. 4A-8). The first transducer may be affixed to the subject's body via an adhesive layer that, optionally, has one or more cut-outs therein (described above), the cut-outs being located over spaces between adjacent electrodes. The first transducer may include an anisotropic material layer electrically coupled to the plurality of electrodes and located between the plurality of electrodes and the subject's body, with the anisotropic material layer optionally having one or more cut-outs therein, the cut-outs being located over spaces between adjacent electrodes.

At step S904, the method 900 may include positioning a second transducer in a second initial position at a second location of the subject's body. The second transducer may include a plurality of electrodes in initial electrode positions and at least one void space located between adjacent electrodes (e.g., as shown in the apparatuses of FIGS. 4A-8). The second transducer may be affixed to the subject's body via an adhesive layer that, optionally, has one or more cut-outs therein, the cut-outs being located over spaces between adjacent electrodes. The second transducer may include an anisotropic material layer electrically coupled to the plurality of electrodes and located between the plurality of electrodes and the subject's body, with the anisotropic material layer optionally having one or more cut-outs therein, the cut-outs being located over spaces between adjacent electrodes.

At step S906, the method 900 may include inducing an electric field between the first transducer located at the first location of the subject's body and the second transducer located at the second location of the subject's body. At step S907, during inducing the electric field, the method 900 may include spreading heat and/or current via an anisotropic material layer from the plurality of electrodes in a plane perpendicular to a direction from the plurality of electrodes to the subject's body. At step S908, the method 900 may include determining whether a first period of time has passed. Upon determining that the first period of time has passed, the method 900 proceeds to step S910. Otherwise, the method 900 returns to step S906. After inducing the electric field for more than the first period of time, the method 900 proceeds to step S910, which may include ceasing the electric field.

At step S912, the method 900 may include moving the first transducer into a first rotation or translation position on the subject's body at the first location, wherein in the first rotation or translation position at least one of the initial electrode positions is now occupied by a space that was present between two electrodes in the first initial position. In some embodiments, in the first rotation or translation position, a void space of the plurality of void spaces of the first transducer may now be located in areas that were previously covered by at least a portion of an electrode for each of the electrodes in the first initial position.

As an example, at step S912, moving the first transducer to the first rotation or translation position may include rotating (S916) the first transducer about its centroid. In particular, moving the first transducer may include rotating the first transducer about its centroid into a first rotation position at the first location of the subject's body, wherein in the first rotation position at least one of the initial electrode positions is now occupied by a space that was present between two electrodes in the first initial position. In some embodiments, in the first rotation position, all areas that were previously covered by an electrode in the first initial position may now be occupied by a space, and vice-versa. As another example, at step S912 moving the first transducer to the first rotation or translation position may include translating (S918) the first transducer with respect to a surface of the subject's body to a first translation position.

At step S914, the method 900 may include moving the second transducer from a second initial position at a second location on the subject's body into a second rotation or translation position on the subject's body (in analogous fashion to that described above for the first transducer in step S912), wherein in the second rotation or translation position at least one of the initial electrode positions is now occupied by a space that was present between two electrodes in the second initial position. In some embodiments, in the second rotation or translation position, a void space of the plurality of void spaces of the second transducer may now be located in areas that were previously covered by at least a portion of an electrode for each of the electrodes in the second initial position. As an example, at step S914 moving the second transducer to the second rotation or translation position may include rotating (S916) the second transducer about its centroid (as described above for movement of the first transducer). As another example, at step S914 moving the second transducer to the second rotation or translation position may include translating (S918) the second transducer with respect to a surface of the subject's body to a second translation position (as described above for movement of the first transducer).

In some embodiments, the step S912 and step S914 may be executed one after another. In some embodiments, the step S912 and step S914 may be executed simultaneously or partially simultaneously.

At step S920, the method 900 may include inducing another electric field between the first transducer and the second transducer. The process returns to step S908 after step S920.

Figure 10:
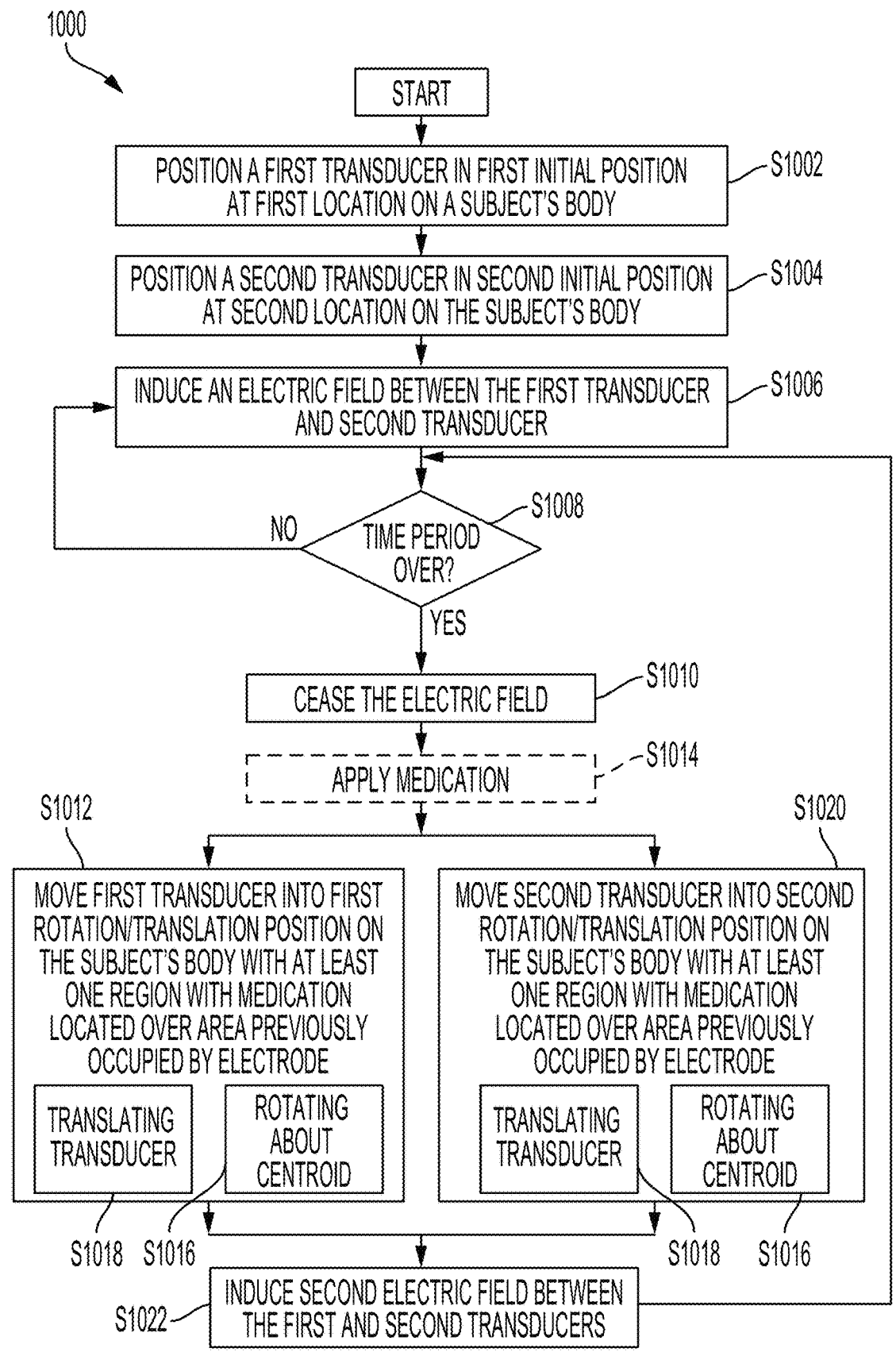
FIG. 10 is a flowchart depicting another example of applying TTFields to a subject's body.

FIG. 10 depicts an example method 1000 of applying TTFields to a subject's body in accordance with the present techniques. The method 1000 begins at step S1002 with positioning a first transducer in a first initial position at a first location of a subject's body. The first transducer may comprise a plurality of electrodes and a medication region located between two adjacent electrodes, the medication region comprising a medication substrate capable of holding a topical medication therein or thereon, and the medication region having no exposed adhesive present thereon. In certain embodiments, the first transducer may include a plurality of medication regions located between adjacent electrodes (e.g., as shown in the apparatuses of FIGS. 4A-8).

At step S1004, the method 1000 may include positioning a second transducer in a second initial position at a second location of the subject's body. The second transducer may comprise a plurality of electrodes in initial electrode positions and a medication region located between two adjacent electrodes, as described above. In certain embodiments, the second transducer may include a plurality of medication regions located between adjacent electrodes (e.g., as shown in the apparatuses of FIGS. 4A-8).

At step S1006, the method 1000 may include inducing an electric field between the first transducer located in a first initial position at the first location of the subject's body and the second transducer in a second initial position located at the second location of the subject's body. At step S1008, the method 1000 may include determining whether a first period of time has passed. Upon determining that the first period of time has passed, the method 1000 proceeds to step S1010. Otherwise, the method 1000 returns to step S1006. After inducing the electric field for more than the first period of time, the method 1000 proceeds to step S1010, which may include ceasing the electric field.

At step S1012, the method 1000 may include moving the first transducer into a first rotation or translation position on the subject's body at the first location, wherein in the first rotation or translation position at least one medication region is holding a topical medication thereon or therein and is in contact with an area of the subject's body that was previously covered by at least a portion of an electrode. In some embodiments, in the first rotation or translation position, a plurality of medication regions of the first transducer may each be located in areas that were previously covered by at least a portion of an electrode for each of the electrodes in the first initial position. As an example, the medication region may include the medication substrate and the topical medication which may be integrated in or on the medication substrate prior to steps S1002 and S1012. As another example, the method 1000 may include, as optional step S1014, applying the topical medication to the medication substrate prior to moving the first transducer into the first rotation or translation position at the first location on the subject's body.

As an example, at step S1012 moving the first transducer to the first rotation or translation position may include rotating (S1016) the first transducer about its centroid. In particular, moving the first transducer may include rotating the first transducer about its centroid into a first rotation position at the first location of the subject's body, wherein in the first rotation position at least one medication region is now located over an area that was previously occupied by at least a portion of an electrode in the first initial position. In some embodiments, in the first rotation position, all areas that were previously covered by an electrode in the first initial position may now be occupied by a medication region, and vice-versa. As another example, at step S1012 moving the first transducer to the first rotation or translation position may include translating (S1018) the first transducer with respect to a surface of the subject's body to a first translation position.

The method 1000 may also include, at step S1020, moving the second transducer from a second initial position at a second location on the subject's body into a second rotation or translation position on the subject's body (in analogous fashion to that described above for the first transducer in step S1012), wherein in the second rotation or translation position, at least one medication region is holding a topical medication thereon or therein and is in contact with an area of the subject's body that was previously covered by at least a portion of an electrode in the second initial position. In some embodiments, in the second rotation or translation position, a plurality of medication regions of the second transducer may each be located in areas that were previously covered by at least a portion of an electrode for each of the electrodes in the second initial position. In some embodiments, for example, the medication region includes the medication substrate and the topical medication which may be integrated in or on the medication substrate prior to steps S1002 and S1020. As another example, the method 1000 may include, as optional step S1014, applying the topical medication to the medication substrate prior to moving the second transducer into the second rotation or translation position at the second location on the subject's body. As an example, at step S1020 moving the second transducer to the second rotation or translation position may include rotating (S1016) the second transducer about its centroid (as described above for movement of the first transducer). As another example, at step S1020 moving the second transducer to the second rotation or translation position may include translating (S1018) the second transducer with respect to a surface of the subject's body to a second translation position (as described above for movement of the first transducer).

In some embodiments, the step S1012 and step S1020 may be executed one after another. In some embodiments, the step S1012 and step S1020 may be executed simultaneously or partially simultaneously.

At step S1022, the method 1000 may include inducing another electric field between the first transducer and the second transducer. The process returns to step S1008 after step S1022.

The invention includes other illustrative embodiments ("Embodiments") as follows.

Embodiment 1: A transducer apparatus for delivering tumor treating fields to a subject's body, the transducer apparatus comprising: an array of electrodes, the array configured to be positioned over the subject's body with a front face of the array facing the subject's body, the array comprising electrode elements positioned in existing electrode positions arranged around a centroid of the array; an anisotropic material layer electrically coupled to the array of electrodes and located on a front side of the front face of the array; and at least one void space in the array of electrodes capable of enclosing an areal footprint equivalent to at least a portion of an areal footprint of at least one existing electrode position, and superimposable on at least a portion of at least one existing electrode position by rotation of the array around the centroid. Embodiment 1A: The transducer apparatus of Embodiment 1, wherein the anisotropic material layer is electrically coupled to the array of electrodes and is located on the front face of the array of electrodes.

Embodiment 2: The transducer apparatus of Embodiment 1, wherein the anisotropic material layer has a front face and a back face, wherein the back face of the anisotropic material layer faces the array of electrodes, wherein the anisotropic material layer has different thermal and/or electrical conductivities in a direction perpendicular to the front face than in directions that are parallel to the front face.

Embodiment 3: The transducer apparatus of Embodiment 1, wherein the anisotropic material layer comprises graphite.

Embodiment 4: The transducer apparatus of Embodiment 1, further comprising at least one layer of conductive adhesive material located on a front facing side of the anisotropic material layer. Embodiment 4A: The transducer apparatus of Embodiment 1, further comprising at least one layer of conductive adhesive material located on a front face of the anisotropic material layer.

Embodiment 5: The transducer apparatus of Embodiment 1, further comprising a first layer of conductive material located between the array of electrodes and a back face of the anisotropic material layer.

Embodiment 6: The transducer apparatus of Embodiment 1, wherein the anisotropic material layer has at least one cut or slit formed through a full thickness of the anisotropic material layer, the cut or slit extending from an outer edge of the anisotropic material layer toward a center portion of the anisotropic material layer when viewed in a direction perpendicular to the face of the array.

Embodiment 7: The transducer apparatus of Embodiment 1, wherein the anisotropic material layer is disposed over the array of electrodes such that the anisotropic material layer covers the electrodes and the at least one void space in the array.

Embodiment 8: The transducer apparatus of Embodiment 1, wherein: the anisotropic material layer substantially covers the array of electrodes, and the anisotropic material layer has one or more cut-outs formed therein, the one or more cut-outs being located over the at least one void space in the array.

Embodiment 9: The transducer apparatus of Embodiment 8, wherein the one or more cut-outs have a closed shape so that the one or more cut-outs are surrounded by the anisotropic material layer when viewed from a direction perpendicular to the face of the array.

Embodiment 10: The transducer apparatus of Embodiment 8, wherein the one or more cut-outs have an open shape so that the one or more cut-outs define one or more concave portions along an outer edge of the anisotropic material layer when viewed from a direction perpendicular to the face of the array.

Embodiment 10A: The transducer apparatus of Embodiment 10, further comprising a substrate for holding the array of electrodes against the subject's body wherein an outer perimeter of the substrate extends beyond the outer edge of the anisotropic material layer and is contoured to match a shape of the outer edge of the anisotropic material layer at one or more concave portions along the outer edge of the anisotropic material layer.

Embodiment 10B: The transducer apparatus of Embodiment 10A, wherein the substrate has at least one cut or slit formed through a full thickness of the substrate, the cut or slit extending from an outer edge of the substrate toward a center portion of the substrate when viewed in a direction perpendicular to the face of the array.

Embodiment 11: The transducer apparatus of Embodiment 1, wherein the at least one void space in the array is capable of enclosing an areal footprint equivalent to at least 40% of an areal footprint of at least one existing electrode position, and superimposable on at least 40% of at least one existing electrode position by rotation of the array around the centroid.

Embodiment 12: The transducer apparatus of Embodiment 1, wherein the at least one void space in the array is capable of enclosing an areal footprint equivalent to at least 90% or at least 95% of an areal footprint of at least one existing electrode position, and superimposable on at least 90% or at least 95% of at least one existing electrode position by rotation of the array around the centroid.

Embodiment 13: The transducer apparatus of Embodiment 1, wherein a sum total of the areal footprints for every void space in the array is approximately 50% of a sum total of areal footprints for every void space and every existing electrode position of the array.

Embodiment 14: The transducer apparatus of Embodiment 1, wherein a sum total of the areal footprints for every void space in the array is equivalent to at least 20% of a sum total of areal footprints for every void space and every existing electrode position of the array.

Embodiment 15: The transducer apparatus of Embodiment 1, wherein the anisotropic material layer comprises pyrolytic graphite, graphitized polymer, or graphite foil made from compressed high purity exfoliated mineral graphite.

Embodiment 16: The transducer apparatus of Embodiment 11 or Embodiment 12, wherein the anisotropic material layer has at least one cut or slit formed through a full thickness of the anisotropic material layer, the cut or slit extending from an outer edge of the anisotropic material layer toward a center portion of the anisotropic material layer when viewed in a direction perpendicular to the face of the array.

Embodiment 17: A transducer apparatus for delivering tumor treating fields to a subject's body, the transducer apparatus comprising: an array of electrodes, the array configured to be positioned over the subject's body with a front face of the array facing the subject's body; an anisotropic material layer electrically coupled to the array of electrodes and located on a front side of the front face of the array; and a void space located between at least one pair of adjacent electrodes of the array; wherein, when viewed from a direction perpendicular to the face of the array, the void space is capable of enclosing an areal footprint equivalent to at least 40%, or at least 45%, or at least 50%, or at least 75%, or at least 90%, or at least 95% of an areal footprint of at least one of the electrodes of the array of electrodes.

Embodiment 18: The transducer apparatus of Embodiment 17, wherein, when viewed from the direction perpendicular to the face of the array: the array comprises electrode elements positioned in existing electrode positions arranged around a centroid of the array, and each tracing an existing electrode footprint; and the void space encompassing an areal footprint defining a potential electrode position, said potential electrode position being arranged around the centroid of the array and tracing a potential electrode footprint; wherein the potential electrode footprint has an identical shape, area, and distance from the centroid, as that of one or more existing electrode footprints, and is in rotational coincidence about the centroid with said one or more existing electrode footprints, such that a rotational shift of the array about the centroid may position the potential electrode position to be coincident upon an existing electrode position.

Embodiment 19: The transducer apparatus of Embodiment 18, wherein the existing electrode footprint of at least one electrode element of the array has a different shape or a different size than the existing electrode footprint of at least one other electrode element of the array.

Embodiment 20: The transducer apparatus of Embodiment 18, wherein at least one single rotation about the centroid results in all potential electrode positions moving to be coincident with positions previously occupied by existing electrode positions.

Embodiment 21: The transducer apparatus of Embodiment 18, wherein the array of electrodes has a non-circular shape.

Embodiment 22: The transducer apparatus of Embodiment 18, wherein each electrode element extends radially outward away from the centroid.

Embodiment 23: The transducer apparatus of Embodiment 17, wherein, when viewed from the direction perpendicular to the face of the array: the array comprises electrodes positioned in existing electrode positions arranged around a centroid of the array; and the void space is superimposable on at least 40%, or at least 45%, or at least 50%, or at least 75%, or at least 90%, or at least 95%, of at least one existing electrode position by rotation of the array around the centroid.

Embodiment 24: The transducer apparatus of Embodiment 17, wherein the anisotropic material layer has a front face and a back face, wherein the back face of the anisotropic material layer faces the array of electrodes, wherein the anisotropic material layer has different thermal and/or electrical conductivities in a direction perpendicular to the front face than in directions that are parallel to the front face.

Embodiment 25: The transducer apparatus of Embodiment 17, further comprising at least one of: conductive adhesive material located on a front facing side of the anisotropic material layer opposite the array of electrodes, or conductive material located between the array of electrodes and a back face of the anisotropic material layer facing the array.

Embodiment 26: The transducer apparatus of Embodiment 17, further comprising at least one of: conductive adhesive material located on a front face of the anisotropic material layer opposite the array of electrodes, or conductive material located between the array of electrodes and a back face of the anisotropic material layer facing the array.

Embodiment 27: The transducer apparatus of Embodiment 17, wherein the anisotropic material layer is disposed over the array of electrodes such that the anisotropic material layer covers the electrodes and the void space.

Embodiment 28: The transducer apparatus of Embodiment 17, wherein: the anisotropic material layer substantially covers the array of electrodes, and the anisotropic material layer has a cut-out formed therein, the cut-out being located over the void space.

Embodiment 29: The transducer apparatus of Embodiment 17, wherein, when viewed from the direction perpendicular to the face of the array: the array comprises electrode elements positioned in existing electrode positions, wherein multiple existing electrode positions are arranged in a line; and the void space is superimposable on at least 40%, or at least 45%, or at least 50%, or at least 75%, or at least 95%, of the areal footprint of each of the existing electrode positions arranged in the line by translation of the array with respect to the subject's body.

Embodiment 30: A method of applying tumor treating fields to a subject's body, the method comprising: locating a first transducer in a first position at a first location on the subject's body, the first transducer comprising: a plurality of electrodes; a void space between at least one pair of adjacent electrodes in the plurality of electrodes; and an anisotropic material layer electrically coupled to the plurality of electrodes and located between the plurality of electrodes and the subject's body; inducing an electric field between the first transducer and a second transducer located at a second location on the subject's body, wherein during inducing the electric field, the anisotropic material layer spreads heat and/or current from the plurality of electrodes in a plane perpendicular to a direction from the plurality of electrodes to the subject's body; after inducing the electric field for more than a first period, ceasing the electric field; moving the first transducer into a second position on the subject's body, wherein in the second position the void space is located over an area of the subject's body that was previously covered by at least a portion of an electrode; and inducing another electric field between the first transducer and the second transducer.

Embodiment 31: The method of Embodiment 30, wherein the anisotropic material layer has different thermal and/or electrical conductivities in a direction perpendicular to a face of the anisotropic material layer than in directions that are parallel to the face of the anisotropic material layer.

Embodiment 32: The method of Embodiment 30, wherein moving the first transducer into the second position comprises rotating the first transducer about a centroid of the first transducer. Embodiment 32A: The method of Embodiment 30, wherein, when viewed from a direction perpendicular to a face of the first transducer array: the plurality of electrodes is positioned in existing electrode positions arranged around a centroid of the transducer; and the void space is superimposable on at least 40%, or at least 45%, or at least 50%, or at least 75%, or at least 90%, or at least 95%, of at least one existing electrode position by rotation of the first transducer about the centroid.

Embodiment 33: The method of Embodiment 30, wherein the first transducer comprises a plurality of void spaces including the void space, wherein each void space of the plurality of void spaces is located between adjacent electrodes of the plurality of electrodes, and wherein in the second position each void space of the plurality of void spaces of the first transducer are located in areas that were previously covered by at least a portion of an electrode.

Embodiment 34: The method of Embodiment 30, wherein the anisotropic material layer covers the void space such that, in the second position, the anisotropic material covers the area of the subject's body that was previously covered by at least a portion of an electrode.

Embodiment 35: The method of Embodiment 30, wherein the anisotropic material layer has a cut-out formed therein located over the void space such that, in the second position, the anisotropic material layer does not cover at least part of the area of the subject's body that was previously covered by at least a portion of an electrode.

Embodiment 36: The method of Embodiment 30, wherein moving the first transducer into the second position comprises translating the first transducer with respect to a surface of the subject's body.

Embodiment 37: A transducer apparatus for delivering tumor treating fields to a subject's body, the transducer apparatus comprising: an array of electrodes, the array configured to be positioned over the subject's body with a face of the array facing the subject's body, said array comprising electrode elements positioned in existing electrode positions arranged around a centroid of the array, and each tracing an existing electrode footprint; and an anisotropic material layer electrically coupled to the array of electrodes and located on a side of the face of the array;

the array also comprising one or more void spaces defining potential electrode positions, said potential electrode positions being arranged around the centroid of the array, each potential electrode position tracing a potential electrode footprint, wherein each potential electrode footprint is in rotational coincidence about the centroid with said one or more existing electrode footprints, such that a rotational shift of the electrode array about the centroid may position at least one potential electrode position to be coincident upon an existing electrode position, thereby providing a resting state for an area of skin beneath at least one electrode after the rotation.

Embodiment 38: The transducer apparatus of Embodiment 37, wherein the anisotropic material layer has a front face and a back face, wherein the back face of the anisotropic material layer faces the array of electrodes, wherein the anisotropic material layer has different thermal and/or electrical conductivities in a direction perpendicular to the front face than in directions that are parallel to the front face.

Embodiment 39: The transducer apparatus of Embodiment 37, further comprising at least one layer of conductive adhesive material located on a front facing side of the anisotropic material layer opposite the array of electrodes, or conductive material located between the array of electrodes and a back face of the anisotropic material layer facing the array.

Embodiment 40: The transducer apparatus of Embodiment 37, further comprising at least one layer of conductive adhesive material located on a front face of the anisotropic material layer opposite the array of electrodes, or conductive material located between the array of electrodes and a back face of the anisotropic material layer facing the array.

Embodiment 41: The transducer apparatus of Embodiment 37, wherein the anisotropic material layer is disposed over the array of electrodes such that the anisotropic material layer covers the electrodes and the one or more void spaces.

Embodiment 42: The transducer apparatus of Embodiment 37, wherein: the anisotropic material layer substantially covers the array of electrodes, and the anisotropic material layer has one or more cut-outs formed therein, the one or more cut-outs being located over the one or more void spaces.

Embodiment 43: The transducer apparatus of Embodiment 37, wherein each potential electrode footprint has an identical shape, area, and distance from the centroid, as that of one or more existing electrode footprints.

Embodiment 44: A method of applying tumor treating fields to a subject's body, the method comprising: positioning a first transducer in a first initial position at a first location of the subject's body, the first transducer comprising a plurality of electrodes in initial electrode positions arranged circumferentially about a centroid of the first transducer and having a space between at least one pair of adjacent electrodes; inducing an electric field between the first transducer and a second transducer located at a second location of the subject's body; spreading heat and/or current output from the plurality of electrodes in a plane substantially perpendicular to a direction from the plurality of electrodes to the subject's body via an anisotropic material layer located between the plurality of electrodes and the subject's body; after inducing the electric field for more than a first period, ceasing the electric field; rotating the first transducer about the centroid into a first rotation position at the first location of the subject's body, wherein in the first rotation position at least one of the initial electrode positions is now occupied by a space that was initially present between two electrodes in the first initial position; and inducing another electric field between the first transducer and the second transducer.

Embodiment 45: A transducer apparatus for delivering tumor treating fields to a subject's body, the transducer apparatus comprising: a substrate layer; an array of electrodes disposed on the substrate layer, the array configured to be positioned over the subject's body with a face of the array facing the subject's body; and an anisotropic material layer electrically coupled to the array of electrodes and located on a side of the array opposite the substrate layer; wherein the anisotropic material layer substantially covers the array of electrodes; wherein the anisotropic material layer has one or more cut-outs formed therein, the one or more cut-outs being located over spaces between adjacent electrodes of the array.

Embodiment 46: A transducer apparatus for delivering tumor treating fields to a subject's body, the transducer apparatus comprising: a substrate layer; an array of electrodes disposed on the substrate layer, the array configured to be positioned over the subject's body with a face of the array facing the subject's body; and an anisotropic material layer electrically coupled to the array of electrodes and located on a side of the array opposite the substrate layer; wherein the anisotropic material layer has at least one cut or slit formed through a full thickness of the anisotropic material layer, the cut or slit extending from an outer edge of the anisotropic material layer toward a center portion of the anisotropic material layer when viewed in a direction perpendicular to the face of the array.

Embodiment 47: The transducer apparatus of Embodiment 46, wherein the substrate layer has at least one cut or slit formed through a full thickness of the substrate layer, the cut or slit extending from an outer edge of the substrate layer toward a center portion of the substrate layer when viewed in the direction perpendicular to the face of the array.

Embodiment 48: The transducer apparatus of Embodiment 47, wherein the cut or slit formed in the substrate layer is at least partially coincident with the cut or slit formed in the anisotropic material layer when viewed from the direction perpendicular to the face of the array.

Embodiment 49: A transducer apparatus for delivering tumor treating fields to a subject's body, the transducer apparatus comprising: an array of electrodes, the array configured to be positioned over the subject's body with a front face of the array facing the subject's body, the array comprising electrode elements positioned in existing electrode positions arranged around a centroid of the array; an anisotropic material layer electrically coupled to the array of electrodes and located on a front side of the front face of the array; wherein the array comprises x' electrodes in existing electrode positions in rotational symmetry about the centroid of the array and which x' electrodes display Cx' point symmetry; and wherein at least one rotation of the array by (360/2x') degrees positions each of the x' electrodes in a new position with less than 40% of any given existing electrode position covered by any portion of any of the x' electrodes in the new position.

Embodiment 50: The transducer apparatus of Embodiment 49, wherein the at least one rotation of the array by (360/2x') degrees positions each of the x' electrodes in a new position with less than 25% of any given existing electrode position covered by any portion of any of the x' electrodes in the new position.

Embodiment 51: The transducer apparatus of Embodiment 49, wherein the at least one rotation of the array by (360/2x') degrees positions each of the x' electrodes in a new position with no overlap of any portion of any of the x' electrodes in the new position over any portion of any given existing electrode position.

Embodiment 52: The transducer apparatus of Embodiment 49, wherein the anisotropic material layer has a front face and a back face, wherein the back face of the anisotropic material layer faces the array of electrodes, wherein the anisotropic material layer has different thermal and/or electrical conductivities in a direction perpendicular to the front face than in directions that are parallel to the front face.

Embodiment 53: The transducer apparatus of Embodiment 49, wherein the anisotropic material layer comprises graphite.

Embodiment 54: The transducer apparatus of Embodiment 49, wherein the anisotropic material layer comprises pyrolytic graphite, graphitized polymer, or graphite foil made from compressed high purity exfoliated mineral graphite.

Embodiment 55: The transducer apparatus of Embodiment 49, further comprising at least one layer of conductive adhesive material located on a front facing side of the anisotropic material layer. Embodiment 55A: The transducer apparatus of Embodiment 49, further comprising at least one layer of conductive adhesive material located on a front face of the anisotropic material layer.

Embodiment 56: The transducer apparatus of Embodiment 49, further comprising a first layer of conductive material located between the array of electrodes and a back face of the anisotropic material layer.

Embodiment 57: The transducer apparatus of Embodiment 49, wherein the anisotropic material layer has at least one cut or slit formed through a full thickness of the anisotropic material layer, the cut or slit extending from an outer edge of the anisotropic material layer toward a center portion of the anisotropic material layer when viewed in a direction perpendicular to the face of the array.

Embodiment 58: The transducer apparatus of Embodiment 49, wherein: the anisotropic material layer substantially covers the array of electrodes, and the anisotropic material layer has one or more cut-outs formed therein.

Embodiment 59: The transducer apparatus of Embodiment 58, wherein the one or more cut-outs have a closed shape so that the one or more cut-outs are surrounded by the anisotropic material layer when viewed from a direction perpendicular to the face of the array.

Embodiment 60: The transducer apparatus of Embodiment 58, wherein the one or more cut-outs have an open shape so that the one or more cut-outs define one or more concave portions along an outer edge of the anisotropic material layer when viewed from a direction perpendicular to the face of the array.

Embodiment 61: The transducer apparatus of Embodiment 60, further comprising a substrate for holding the array of electrodes against the subject's body wherein an outer perimeter of the substrate extends beyond the outer edge of the anisotropic material layer and is contoured to match a shape of the outer edge of the anisotropic material layer at one or more concave portions along the outer edge of the anisotropic material layer.

Embodiment 62: The transducer apparatus of Embodiment 61, wherein the substrate has at least one cut or slit formed through a full thickness of the substrate, the cut or slit extending from an outer edge of the substrate toward a center portion of the substrate when viewed in a direction perpendicular to the face of the array.

Embodiments illustrated under any heading or in any portion of the disclosure may be combined with embodiments illustrated under the same or any other heading or other portion of the disclosure unless otherwise indicated herein or otherwise clearly contradicted by context. For example, and without limitation, embodiments described in dependent claim format for a given embodiment (e.g., the given embodiment described in independent claim format) may be combined with other embodiments (described in independent claim format or dependent claim format).

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

What is claimed is:

1. A transducer apparatus for delivering tumor treating fields to a subject's body, the transducer apparatus comprising:
    an array of electrodes, the array configured to be positioned over the subject's body with a front face of the array facing the subject's body, the array comprising electrode elements positioned in existing electrode positions arranged around a centroid of the array;
    an anisotropic material layer electrically coupled to the array of electrodes and located on a front side of the front face of the array; and
    at least one void space in the array of electrodes capable of enclosing an areal footprint equivalent to at least a portion of an areal footprint of at least one existing electrode position, and superimposable on at least a portion of at least one existing electrode position by rotation of the array around the centroid.

2. The transducer apparatus of claim 1, wherein the anisotropic material layer has a front face and a back face, wherein the back face of the anisotropic material layer faces the array of electrodes, wherein the anisotropic material layer has different thermal and/or electrical conductivities in a direction perpendicular to the front face than in directions that are parallel to the front face.

3. The transducer apparatus of claim 1, wherein the anisotropic material layer comprises graphite.

4. The transducer apparatus of claim 1, further comprising at least one layer of conductive adhesive material located on a front facing side of the anisotropic material layer.

5. The transducer apparatus of claim 1, further comprising a first layer of conductive material located between the array of electrodes and a back face of the anisotropic material layer.

6. The transducer apparatus of claim 1, wherein the anisotropic material layer has at least one cut or slit formed through a full thickness of the anisotropic material layer, the cut or slit extending from an outer edge of the anisotropic material layer toward a center portion of the anisotropic material layer when viewed in a direction perpendicular to the front face of the array.

7. The transducer apparatus of claim 1, wherein the anisotropic material layer is disposed over the array of electrodes such that the anisotropic material layer covers the electrodes and the at least one void space in the array.

8. The transducer apparatus of claim 1, wherein:
    the anisotropic material layer substantially covers the array of electrodes, and
    the anisotropic material layer has one or more cut-outs formed therein, the one or more cut-outs being located over the at least one void space in the array.

9. The transducer apparatus of claim 8, wherein the one or more cut-outs have a closed shape so that the one or more cut-outs are surrounded by the anisotropic material layer when viewed from a direction perpendicular to the front face of the array.

10. The transducer apparatus of claim 8, wherein the one or more cut-outs have an open shape so that the one or more cut-outs define one or more concave portions along an outer edge of the anisotropic material layer when viewed from a direction perpendicular to the front face of the array.

11. The transducer apparatus of claim 10, further comprising a substrate for holding the array of electrodes against the subject's body wherein an outer perimeter of the substrate extends beyond the outer edge of the anisotropic material layer and is contoured to match a shape of the outer edge of the anisotropic material layer at one or more concave portions along the outer edge of the anisotropic material layer.

12. The transducer apparatus of claim 11, wherein the substrate has at least one cut or slit formed through a full thickness of the substrate, the cut or slit extending from an outer edge of the substrate toward a center portion of the substrate when viewed in a direction perpendicular to the front face of the array.

13. The transducer apparatus of claim 1, wherein the at least one void space in the array is capable of enclosing an areal footprint equivalent to at least 40% of an areal footprint of at least one existing electrode position, and superimposable on at least 40% of at least one existing electrode position by rotation of the array around the centroid.

14. The transducer apparatus of claim 1, wherein a sum total of the areal footprints for every void space in the array is equivalent to at least 20% of a sum total of areal footprints for every void space and every existing electrode position of the array.

15. A transducer apparatus for delivering tumor treating fields to a subject's body, the transducer apparatus comprising:
an array of electrodes, the array configured to be positioned over the subject's body with a front face of the array facing the subject's body;
an anisotropic material layer electrically coupled to the array of electrodes and located on a front side of the front face of the array; and
a void space located between at least one pair of adjacent electrodes of the array;
wherein, when viewed from a direction perpendicular to the front face of the array, the void space is capable of enclosing an areal footprint equivalent to at least 40% of an areal footprint of at least one of the electrodes of the array of electrodes.

16. The transducer apparatus of claim 15, wherein, when viewed from the direction perpendicular to the front face of the array:
the array comprises electrode elements positioned in existing electrode positions arranged around a centroid of the array, and each tracing an existing electrode footprint; and
the void space encompassing an areal footprint defining a potential electrode position, said potential electrode position being arranged around the centroid of the array and tracing a potential electrode footprint;
wherein the potential electrode footprint has an identical shape, area, and distance from the centroid, as that of one or more existing electrode footprints, and is in rotational coincidence about the centroid with said one or more existing electrode footprints, such that a rotational shift of the array about the centroid may position the potential electrode position to be coincident upon an existing electrode position.

17. The transducer apparatus of claim 1, wherein the array comprising electrode elements includes at least 3 and at most 6 electrode elements.

18. The transducer apparatus of claim 17, wherein the array comprising electrode elements has 3 electrode elements.

19. The transducer apparatus of claim 15, wherein the array of electrodes includes at least 3 and at most 6 electrodes.

20. The transducer apparatus of claim 19, wherein the array of electrodes has 3 electrodes.

* * * * *